US007817264B2

United States Patent
Sanada

(10) Patent No.: US 7,817,264 B2
(45) Date of Patent: Oct. 19, 2010

(54) METHOD FOR PREPARING FOCUS-ADJUSTMENT DATA FOR FOCUSING LENS SYSTEM OF OPTICAL DEFECT-INSPECTION APPARATUS, AND FOCUS ADJUSTMENT WAFER USED IN SUCH METHOD

(75) Inventor: Kenichi Sanada, Yamagata (JP)

(73) Assignee: NEC Electronics Corporation, Kawasaki, Kanagawa (JP)

( * ) Notice: Subject to any disclaimer, the term of this patent is extended or adjusted under 35 U.S.C. 154(b) by 191 days.

(21) Appl. No.: 11/730,571

(22) Filed: Apr. 2, 2007

(65) Prior Publication Data

US 2007/0229811 A1    Oct. 4, 2007

(30) Foreign Application Priority Data

Apr. 3, 2006    (JP)    ............................. 2006-102564
Mar. 29, 2007   (JP)    ............................. 2007-086589

(51) Int. Cl.
    *G01N 21/00*    (2006.01)
(52) U.S. Cl. ................. 356/237.4; 356/237.3
(58) Field of Classification Search ... 356/237.1–237.6, 356/239.3–239.8, 600–601, 243.7, 243.4, 356/394, 243.6; 348/87; 250/559.2, 559.3, 250/559.39, 559.4–559.46; 382/144–145, 382/148–149, 151, 169, 170, 218, 274, 294; 438/16; 702/40, 159, 172; 700/110, 121

See application file for complete search history.

(56) References Cited

U.S. PATENT DOCUMENTS

| 4,626,101 | A  | * | 12/1986 | Ogawa et al. ............. 356/237.2 |
| 6,344,897 | B2 | * | 2/2002  | Miyazaki et al. ......... 356/237.4 |
| 6,801,650 | B1 | * | 10/2004 | Kikuchi et al. .............. 382/145 |
| 6,890,859 | B1 | * | 5/2005  | Bamnolker et al. ......... 438/700 |
| 2001/0020194 | A1 | * | 9/2001 | Takagi et al. ................ 700/109 |
| 2006/0030060 | A1 | * | 2/2006 | Noguchi et al. ............... 438/14 |
| 2007/0035725 | A1 | * | 2/2007 | Takahashi et al. ........ 356/237.1 |

FOREIGN PATENT DOCUMENTS

JP    2000-58606    2/2000
JP    2003-271927   9/2003

* cited by examiner

*Primary Examiner*—Gregory J Toatley, Jr.
*Assistant Examiner*—Tri T Ton
(74) *Attorney, Agent, or Firm*—McGinn IP Law Group, PLLC

(57) ABSTRACT

In a method for preparing focus-adjustment data for a focusing lens system of an optical defect-inspection apparatus, a wafer having a plurality of defects is positioned in place with respect to a focal plane defined by the focusing lens system at a positioning step, and the detects on the wafer are optically and electronically detected at a detecting step. Then, defects having a predetermined size are extracted among the detected defects at extracting step, and a number of the extracted defects is counted as defect-number data. The positioning, detecting, extracting and counting steps are repeated whenever the focus-adjustment wafer is relatively shifted from the focal plane by a predetermined distance, and a defect-number distribution is produced based on the defect-number data thus obtained.

13 Claims, 20 Drawing Sheets

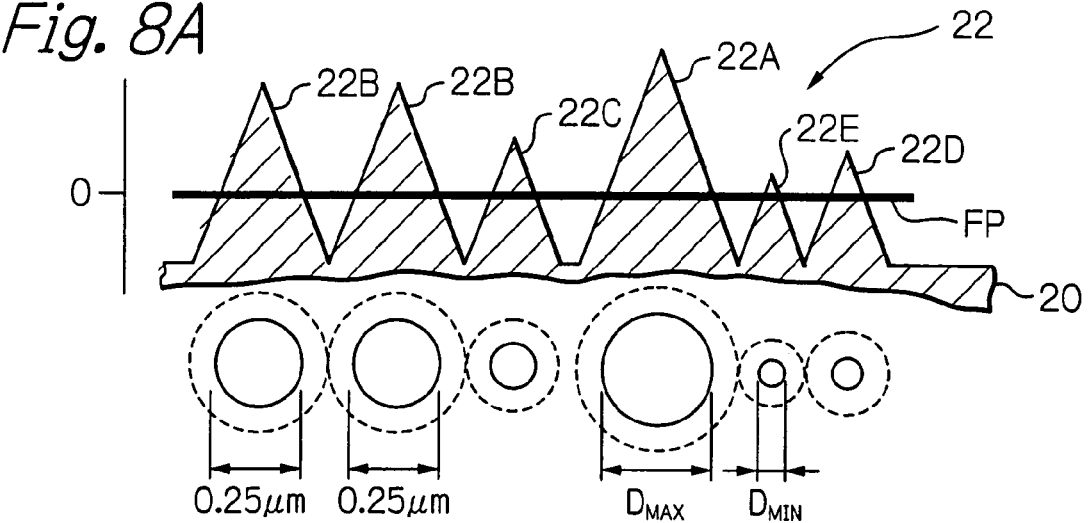
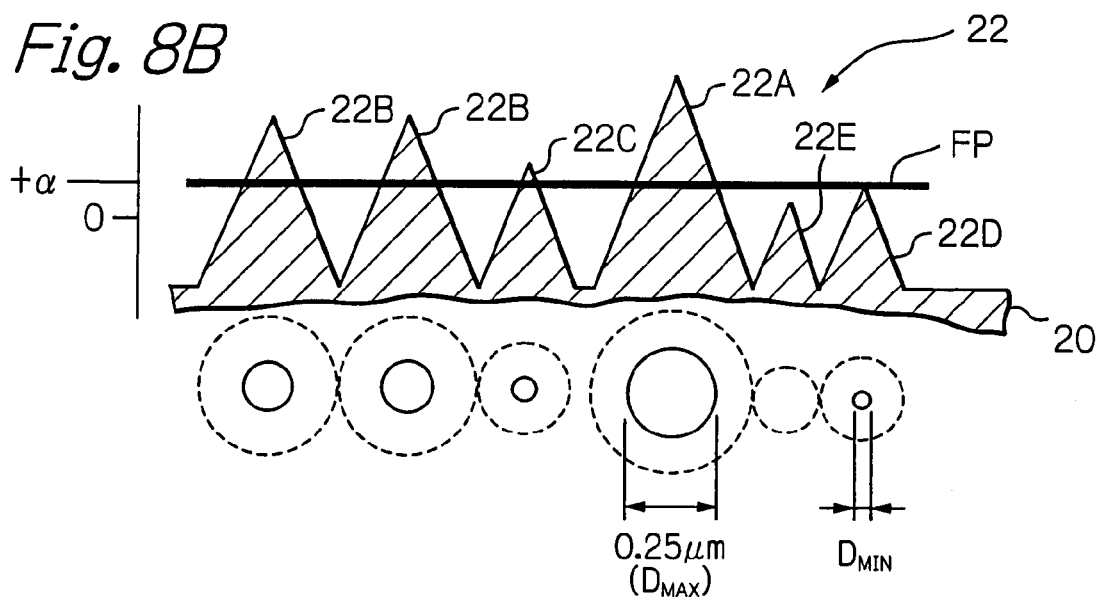
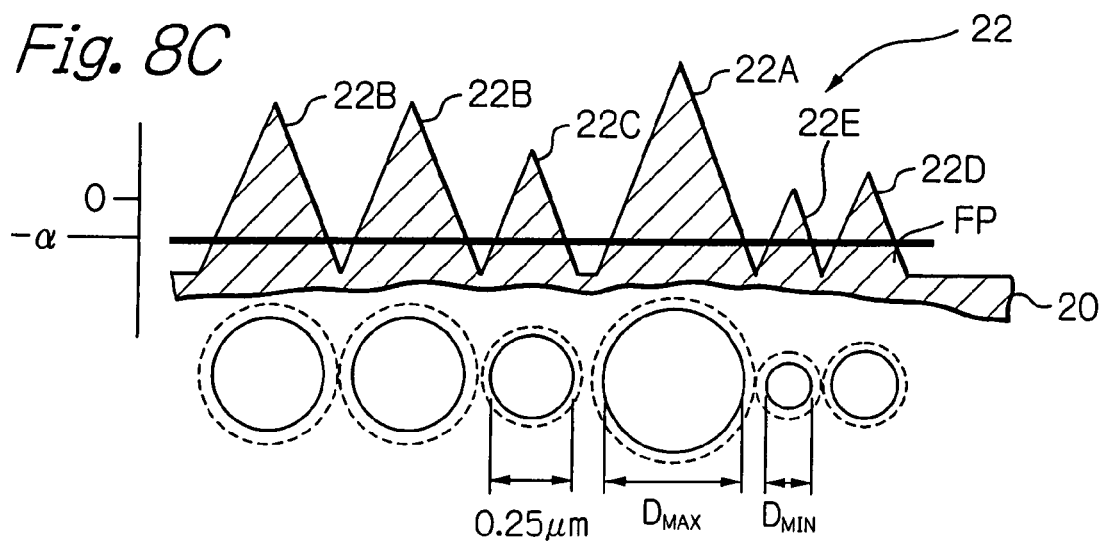

METHOD FOR PREPARING FOCUS-ADJUSTMENT DATA FOR FOCUSING LENS SYSTEM OF OPTICAL DEFECT-INSPECTION APPARATUS, AND FOCUS ADJUSTMENT WAFER USED IN SUCH METHOD

BACKGROUND OF THE INVENTION

1. Field of the Invention

The present invention relates to a method for preparing focus-adjustment data for a focusing lens system of an optical defect-inspection apparatus, and a focus-adjustment wafer used in such a method. Also, the present invention relates to an optical defect-inspection apparatus which is constituted so as to carry out the method.

2. Description of the Related Art

Conventionally, there are various types of optical defect-inspection apparatus for inspecting a semiconductor wafer to detect defects on each of the semiconductor chips on the semiconductor wafer, as disclosed in, for example, JP-2003-271927 A.

The optical defect-inspection apparatus includes an optical image sensing unit for optically sensing each of the semiconductor chips to thereby produce chip image data, and an image-processing unit for electronically processing the chip image data to thereby detect defects on the semiconductor wafer based on the processed image data.

Also, JP-2000-058606 A discloses a reference wafer used in a light-scattering inspection apparatus to detect and quantify scratch defects which are made in a semiconductor wafer when the silicon wafer is subjected to a chemical mechanical polishing (CMP) process. Namely, the reference wafer has a plurality of dummy scratch defects formed in a surface thereof, and each of the dummy scratch defects has known width and depth. The dummy scratch defects are previously optically sensed by using an optical scanning unit of the light-scattering inspection apparatus to thereby acquire width and depth data on each of the dummy scratch defects.

When the semiconductor wafer subjected to the CMP process is inspected in the light-scattering inspection apparatus to detect scratch defects, each of the detected scratch defects is compared with the width and depth data of the dummy scratch defects to thereby quantify the detected scratch defect concerned.

At any rate, the optical defect-inspection apparatus and the light-scattering inspection apparatus have an optical scanning system for scanning a semiconductor wafer with a light beam, and the light beam is focused on the semiconductor wafer by using an optical focusing lens system. Namely, the semiconductor wafer is positioned in place with respect to a focal plane defined by the optical focusing lens system.

SUMMARY OF THE INVENTION

It has now been discovered that the above-mentioned prior arts have problems to be solved as mentioned hereinbelow.

In particular, with a recent advance of integration and miniaturization of semiconductor chips on a semiconductor wafer, patterns on semiconductor chips have become increasingly smaller, and thus it is necessary to detect finer defects on the semiconductor chips. Thus, a positional adjustment of a semiconductor wafer with respect to the focal plane becomes stricter. In short, although it is necessary to more strictly and precisely carry out the positional adjustment of the semiconductor wafer with respect to the focal plane before the fine defects can be properly detected, in reality, the strict and precise adjustment is very difficult due to aging of the aforesaid inspection apparatuses, and the effects of environmental changes, as discussed in detail hereinafter.

In accordance with a first aspect of the present invention, there is provided a method for preparing focus-adjustment data for a focusing lens system of an optical defect-inspection apparatus. The method comprises steps of: positioning a wafer having a plurality of defects in place with respect to a focal plane defined by the focusing lens system; optically and electronically detecting the detects on the wafer; extracting defects, having a predetermined size, among the detected defects; counting a number of the extracted defects as defect-number data; repeating the positioning step, the detecting step, the extracting step and the counting step whenever the wafer is relatively shifted from the focal plane by a predetermined distance; and producing a defect-number distribution based on the defect-number data thus obtained.

The method may further comprise steps of: calculating a peak value of the defect-number distribution; and calculating a shift value, shifted from an original position of the focal plane, based on the peak value. Alternatively, the method may further comprise steps of: calculating a peak value of the defect-number distribution; and calculating a vertical offset value and a horizontal offset value by comparing the peak value with a peak value of a defect-number distribution obtained in a similar manner to the method in a defect-inspection apparatus which is identical to the defect-detection apparatus.

In accordance with a second aspect of the present invention, there is provided a focus-adjustment wafer used in an optical defect-inspection apparatus to carry out a focus-adjustment of a focusing lens system of the optical defect-inspection apparatus. The focus-adjustment wafer includes a wafer substrate having a plurality of chip areas defined thereon, and a plurality of defects formed on or in each of the chip areas on the wafer substrate. The defects have various defect sizes falling within a size range, and the distribution of the defects in various sizes has at least one maximum value in the middle of the size range.

When a silicon wafer to be inspected in the defect-inspection apparatus has real defects having sizes falling within a size range between 0.1 µm and 0.3 µm, the size range may be from about 0.05 µm to about 0.5 µm. Also, the defects are formed on or in the wafer substrate at a density falling within a range between several/cm$^2$ and hundreds/cm$^2$.

Preferably, each of the defects may be configured as either a cone-shaped defect or a pyramid-shaped defect. In this case, either the cone-shaped defect or the pyramid-shaped defect may be formed as a solid defect on each of the chip areas. Also, either the cone-shaped defect or the pyramid-shaped defect may be formed as a hollow defect in each of the chip areas.

The focus-adjustment wafer may further include a plurality of patterns formed on or in the at least one chip area on the wafer substrate. Each of the patterns may be configured as a rectangular-like parallelepiped pattern. The rectangular-like parallelepiped pattern may be formed as a solid pattern on each of the chip areas. Also, the rectangular-like parallelepiped pattern may be formed as a hollow pattern on each of the chip areas.

When the chip areas are defined as first chip areas, the wafer substrate may have a plurality of second chip areas defined thereon. In this case, the focus-adjustment wafer further includes a plurality of patterns formed on or in each of the second chip areas on the wafer substrate. Preferably, the first chip areas and the second chip areas are alternately arranged side by side. Each of the patterns may be configured as a circular column, with the defects on each of the first chip areas being configured as a cone-shaped defect having a size equivalent to a diameter of said circular column. A part of the defects may be formed as solid defects, and the remaining part may be formed as hollow defects. Also, a part of the patterns may be formed as solid patterns, and the remaining part may be formed as hollow patterns.

In accordance with a third aspect of the present invention, there is provided an optical defect-inspection apparatus which comprises: a system control unit; a movable wafer stage for setting a wafer thereon; a stage control unit that is driven under control of the system control unit to thereby control movement of the movable wafer stage; an optical image-sensing unit that senses image data of the wafer; and an image-processing unit that processes the image data. The system control unit detects defects on the wafer based on the processed image data, and is provided with a program that carries out the aforesaid method.

BRIEF DESCRIPTION OF THE DRAWINGS

The present invention will be more clearly understood from the description set forth below, as compared with the prior arts, with reference to the accompanying drawings, wherein:

FIGS. 8A, 8B and 8C are explanatory views for explaining how to prepare focus-adjustment data for the focusing-lens system included in the defect-inspection apparatus of FIG. 4;

DESCRIPTION OF THE PREFERRED EMBODIMENTS

Before description of embodiments of the present invention, for better understanding of the present invention, with reference to FIG. 1 and FIGS. 2A and 2B, a prior art defect-inspection apparatus for a semiconductor wafer, as disclosed in JP-2003-271927 A, will be explained below.

Figure 1:
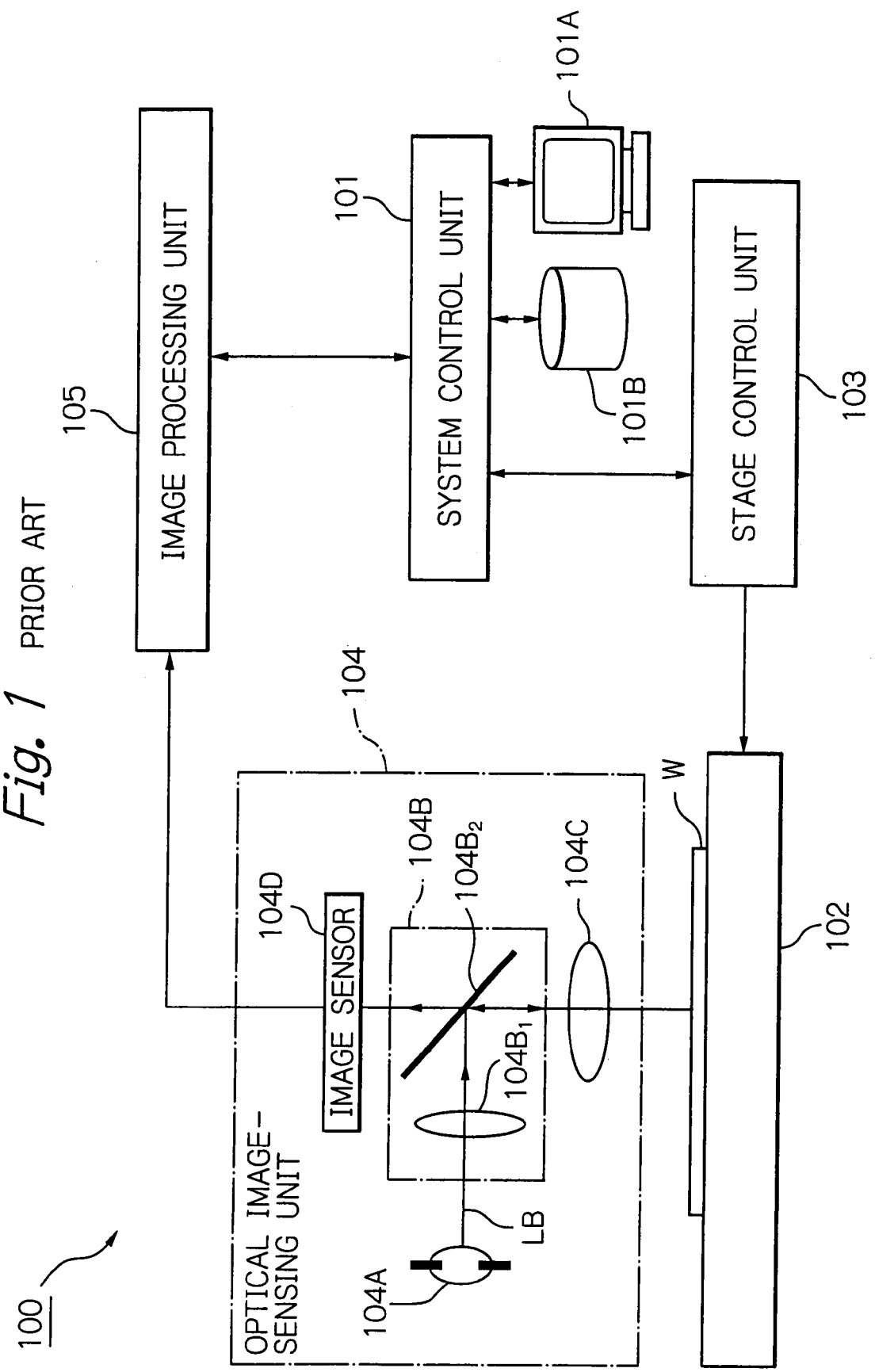
FIG. 1 is a block diagram of a prior art optical defect-inspection apparatus for inspecting a semiconductor wafer to determine whether or not there are defects therein.

First, referring to FIG. 1 which is a block diagram of the prior art optical defect-inspection apparatus, the optical defect-inspection apparatus is generally indicated by reference 100.

The defect-inspection apparatus 100 includes a system control unit 101 which contains a microcomputer having a central processing unit (CPU), a read-only memory (ROM) for storing various programs and constants, a random-access memory (RAM) for storing temporary data, an input/output (I/O) interface circuit and so on. Also, the system control unit 101 is provided with a user interface such as a personal computer 101A, an external memory 101B such as a hard disk unit and so on.

The defect-inspection apparatus 100 also includes a movable wafer stage 102, and a stage control unit 103 for moving vertically and horizontally the movable wafer stage 102 under control of the system control unit 101. A semiconductor wafer W such as a silicon wafer to be inspected is detachably set on the wafer stage 102. Note that a plurality of semiconductor chips (not shown) are already produced in a front surface of the silicon wafer W, and that the semiconductor chips are identical to each other.

The defect-inspection apparatus 100 further includes an optical image-sensing unit 104 which is operated under control of the system control unit 101 so as to optically sense the semiconductor chips produced on the silicon wafer W.

The optical image-sensing unit 104 includes a light source 104A such as a laser light source for emitting a light beam LB, an optical illumination system 104B having a condenser or collimator lens 104B$_1$ and a half mirror 104B$_2$ for directing the light beam LB toward the silicon wafer W, and a focusing lens system 104C for focusing the light beam LB on the silicon wafer W so that the silicon wafer W is illuminated with the focused light beam LB.

Although the focusing lens system 104C is represented by only one lens in FIG. 1, in reality, it includes a plurality of lenses, some of which are movable along an optical axis thereof, so that an optical power of the focusing lens system 104C can be varied. Namely, the focusing lens system 104C is suitably driven by the system control unit 101 so that a given optical power may be set in the focusing lens system 104C. Also, by the setting of the optical power, a focal plane, on which the light beam LB is focused, is automatically defined.

Whenever the optical power of the focusing lens system 104C is varied, the wafer stage 102 is vertically moved by the stage control unit 103 with respect to the optical image-sensing unit 104 so that the silicon wafer W to be inspected is positioned in place with respect to the focal plane.

After the silicon wafer W to be inspected is positioned in place with respect to the focal plane, the wafer stage 102 is horizontally moved by driving the stage control unit 103 under control of the system control unit 101, so that the semiconductor chips on the silicon wafer W are scanned with the light beam LB.

The optical image-sensing unit 104 further includes an image sensor 104D such as a charge-coupled device (CCD) sensor, which is driven under control of the system control unit 101, and which receives the light beam LB reflected by the silicon wafer W through the half mirror 104B$_2$ during the scanning of the silicon wafer W with the light beam LB. The image sensor 104D sequentially converts the received light beam LB into image signals.

The defect-inspection apparatus 100 further includes an image-processing unit 105 which is driven under control of the system control unit 101, and which sequentially receives the image signals from the image sensor 104D of the optical image-sensing unit 104. Note, the image-processing unit 105 may be formed as a digital signal processor (DSP).

In the image-processing unit 105, digital chip images of the semiconductor chips on the silicon wafer W are produced one after another based on the image signals, and a trailing one of two consecutive digital chip images is matched and compared with a leading one thereof to thereby produce a comparative chip image. The comparative chip image is fed from the image-processing unit 105 to the system control unit 101 in which it is inspected whether or not there are defects in the trailing digital chip image based on the comparative chip image. The inspection results may be displayed together with the comparative chip image on the monitor of the personal computer 101A, if necessary, and may stored in the external memory 101B, if necessary.

Figure 2B:
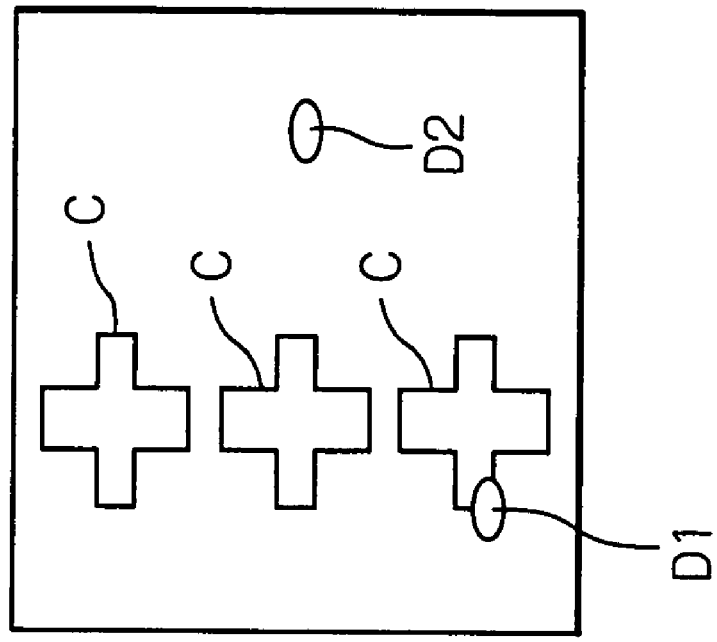
FIGS. 2A and 2B are schematic and conceptual views showing two consecutive chip images produced in an image-processing unit of the optical defect-inspection apparatus of FIG. 1.
Figure 2A:
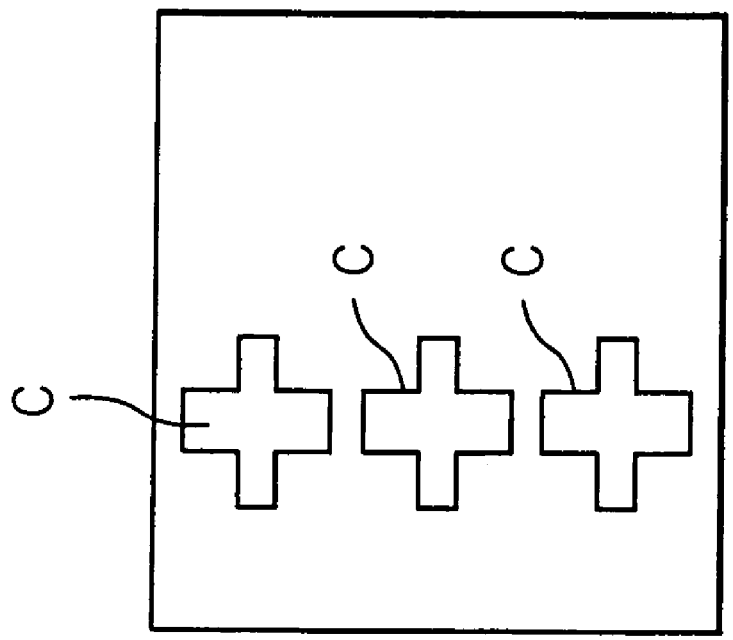

Referring to FIG. 2A which shows an example of the leading one of the aforesaid consecutive digital chip images, the leading digital chip image has only cross patterns C. In this example, although the leading digital chip image has no defect, it may have defects.

On the other hand, referring to FIG. 2B which shows an example of the trailing digital chip image of the aforesaid consecutive digital chip images, the trailing digital chip image has not only cross patterns C but also defects D1 and D2. In this example, the defect D1 is shown as a dent in an edge of the cross pattern C concerned, and the defect D2 is shown as a dust particle adhered on the semiconductor chip concerned.

In the image-processing unit 105 of FIG. 1, the leading chip image of FIG. 2A is used as a reference chip image, and is compared with the trailing chip image of FIG. 2B, whereby it is inspected that the trailing chip image has the defects D1 and D2 in the system control unit 101. When the next digital chip image is produced based on the image signal fed from the image sensor 104D of the optical image-sensing unit 104, the trailing chip image of FIG. 2B is used as a reference chip image, and is compared with the next chip image to thereby produce a comparative chip image.

With a recent advance of miniaturization and integration of semiconductor chips, patterns on the semiconductor chip become increasingly smaller, and thus it is necessary to detect finer defects on the semiconductor chip. In this case, a focus-adjustment of the focusing lens system 104C becomes stricter. Namely, the focusing of the focusing lens system 104C can more strictly carried out before the fine defects can be properly detected. Nevertheless, it is very difficult to strictly and precisely carry out the focus-adjustment of the focusing lens system 104C due to aging of the stage control unit 103, the optical illumination system 104B and so on. Also, the strict and precise focus-adjustment is affected by environmental changes.

Figure 3B:
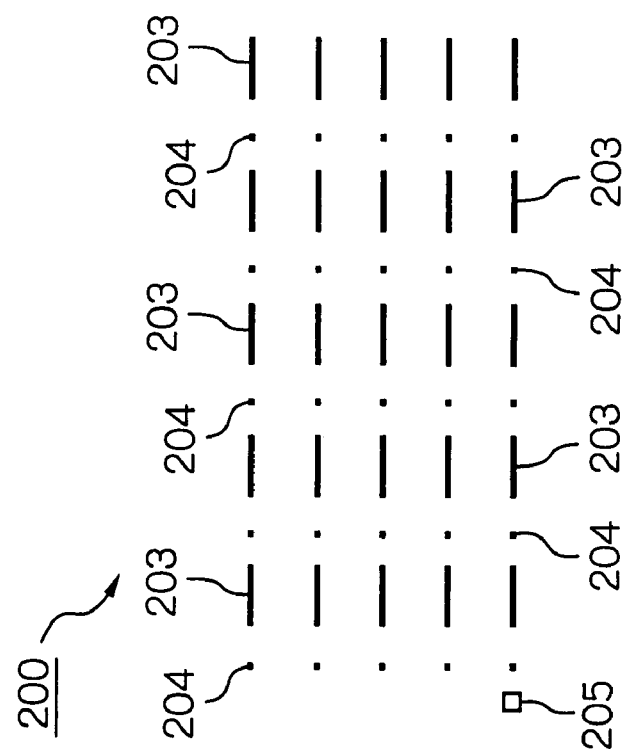
FIG. 3B is a detailed view of one of the blocks of FIG. 3A.
Figure 3A:
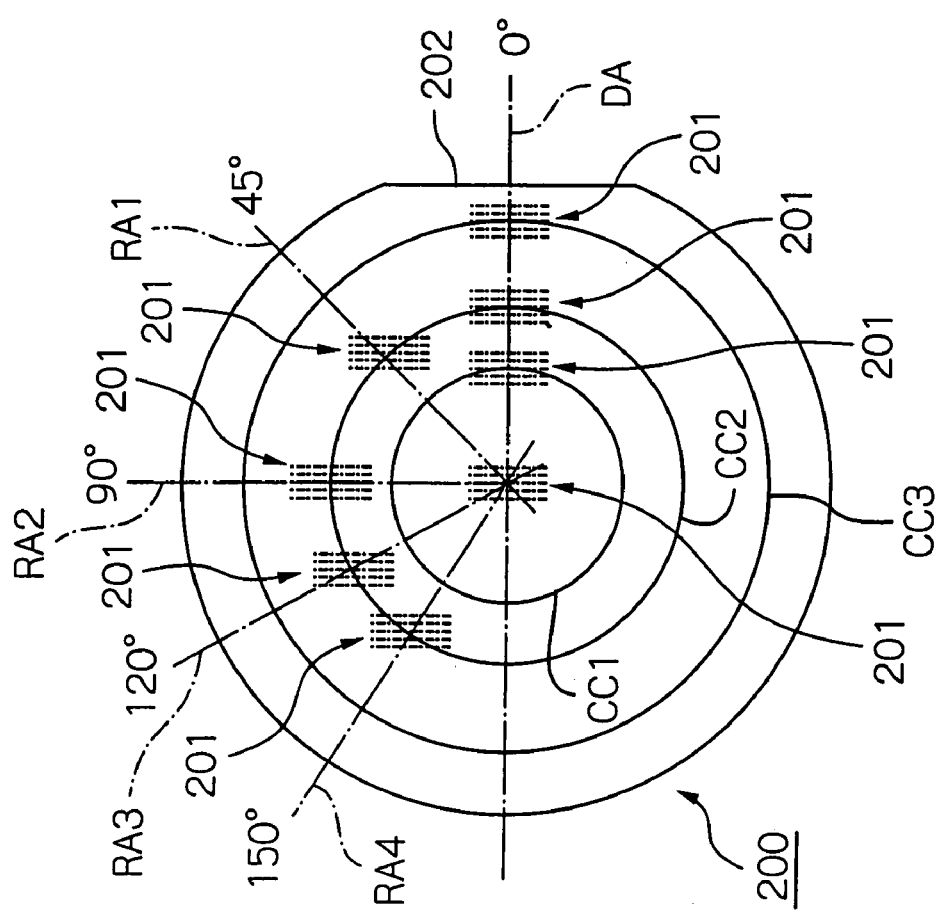
FIG. 3A is a plan view of a prior art reference wafer used in a light-scattering inspection apparatus having a plurality of blocks, each of which is composed of twenty five dummy scratch defects formed therein.

Referring to FIG. 3A which is a plan view of a prior art reference wafer, as disclosed in JP-2000-058606 A, the reference wafer is generally indicated by reference numeral 200.

The reference wafer 200 is used in a light-scattering inspection apparatus (not shown) to detect and quantify scratch defects which are made in a semiconductor wafer such as a silicon wafer when the silicon wafer is subjected to a chemical mechanical polishing (CMP) process. To this end, the reference wafer 200 has eight blocks 201, each of which is composed of twenty five pits or dummy scratch defects formed in a surface of the reference wafer 200.

For the sake of convenience of explanation, three concentric circles CC1, CC2 and CC3 are defined on the surface of the reference wafer 200. Also, a diametrical axis DA and four radial axes RA1, RA2, RA3 and RA4 are defined on a surface of the reference wafer 200. Namely, the diametrical axis DA passes through the center of the reference wafer 200, and crosses the center of an orientation flat 202 of the reference wafer 200, and the radial axes RA1, RA2, RA3 and RA4 are at respective angles of 45, 90, 120 and 150 degrees with respect to the diametrical axis DA.

One of the blocks 201 is arranged at the center of the reference wafer 200. Three others of the other blocks 201 are arranged at respective locations at which the concentric circles CC1, CC2 and CC3 intersect with the diametrical axis DA. Also, another of the blocks 201 is arranged at a location at which the concentric circle CC2 intersects with the radial axis RA1, and yet another of the blocks 201 is arranged at a location at which the concentric circle CC2 intersects with the radial axis RA2. Further, still yet another of the blocks 201 is arranged at a location at which the concentric circle CC2 intersects with the radial axis RA3, and the remaining block 201 is arranged at a location at which the concentric circle CC2 intersects with the radial axis RA4.

Referring to FIG. 3B which is a detailed view of one of the blocks 201, the twenty five dummy scratch defects are indicated by reference 203, and are arranged in a 5×5 matrix manner. The twenty five dummy scratch defects 203 have different widths and depths which fall within a range between 0.025 μm and 0.4 μm.

Also, each of blocks 201 has twenty five square pits 204 formed in the surface of the reference wafer 200 so as to be associated with the respective dummy scratch defects 203. The square pits 204 have different sizes, each of which represents both the width and the depth of the corresponding the dummy scratch defect 203.

Further, each of blocks 201 has a 20×20 μm pit 205 which formed in the surface of the reference wafer 200 at a corner of the block 201.

The aforesaid light-scattering inspection apparatus (not shown) includes a rotary stage for setting the reference wafer 200 thereon, an optical scanning unit for scanning the reference wafer 200 with a light beam, and an optical sensor for detecting the light beam reflected from the reference wafer 200.

In operation, first, the reference wafer 200 is set on the rotary stage, and then is searched for one of the blocks 201 by using the optical sensor. At this time, the 20×20 μm pit 205 serves as a mark for searching the reference wafer 200 for the corresponding block 201. Then, the dummy scratch defects 203 with the pits 204 included in the block 201 concerned are scanned with the light beam which is emitted from the optical scanning unit, and the optical sensor detects the dummy scratch defects 203 to thereby acquire width and depth data on each of the dummy scratch defects 203.

After the width and depth information are acquired, a silicon wafer subjected to a CMP process is set on the rotary stage, and the silicon wafer is scanned with the light beam which is emitted from the optical scanning unit, and scratch defects, which are caused by the CMP process, are detected by the optical sensor. Each of the detected scratch defects is compared with the width and depth data to thereby quantify the detected scratch defect concerned.

With the recent advance of miniaturization and integration of semiconductor chips, it is necessary to detect finer scratch defects, and thus a focus-adjustment of the optical scanning unit becomes stricter. Nevertheless, it is very difficult to strictly and precisely carry out the focus-adjustment of the optical scanning unit for the same reasons as in the above-mentioned.

Optical Defect-Inspection Apparatus

Figure 4:
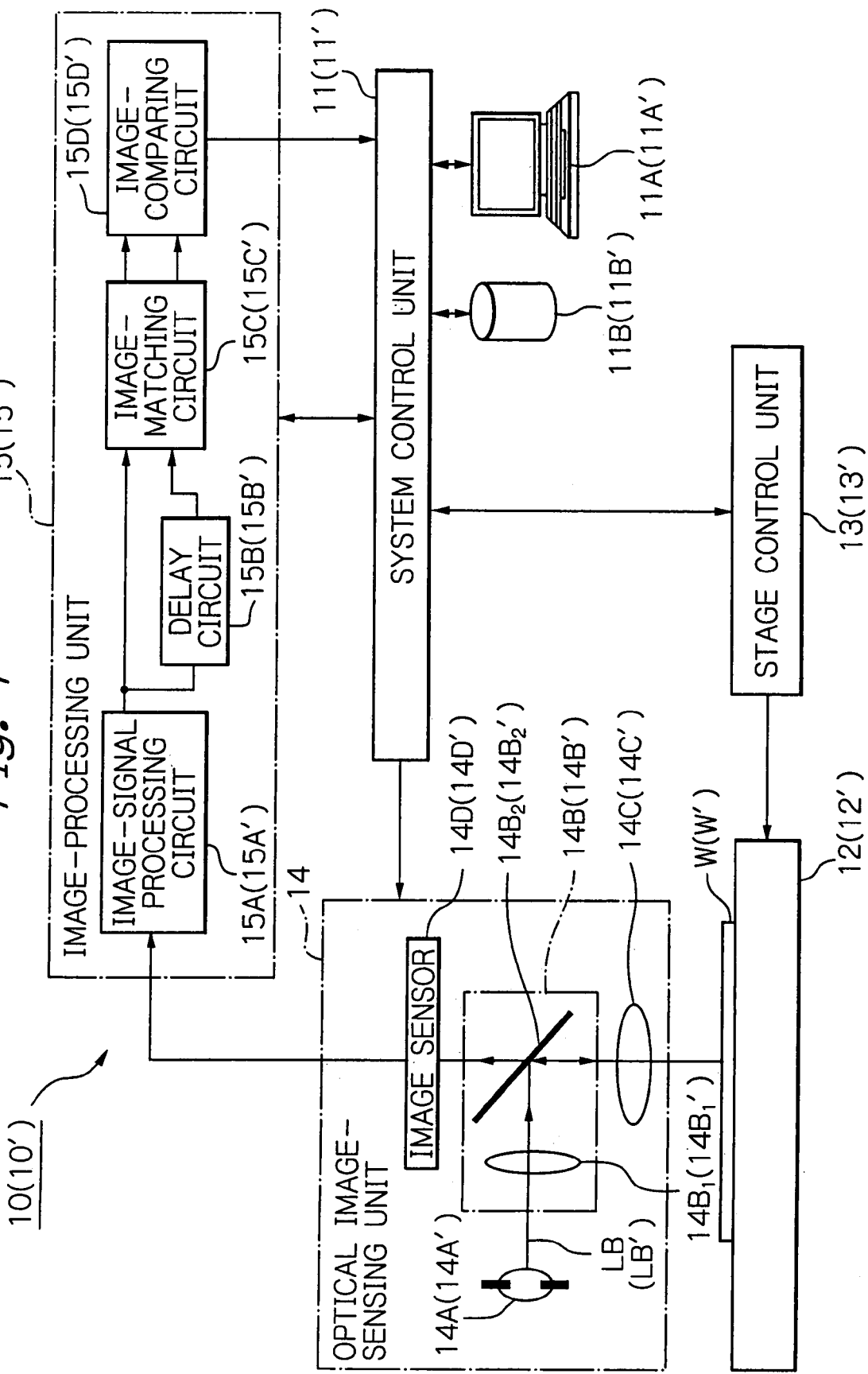
FIG. 4 is a block diagram of a defect-inspection apparatus according to the present invention.

With reference to FIG. 4 which is a block diagram of the optical defect-inspection apparatus for a semiconductor wafer according to the present invention, the optical defect-inspection apparatus is generally indicated by reference 10.

The optical defect-inspection apparatus 10 includes a system control unit 11 which contains a microcomputer having a central processing unit (CPU), a read-only memory (ROM) for storing various programs and constants, a random-access memory (RAM) for storing temporary data, an input/output (I/O) interface circuit and so on. Also, the system control unit 11 is provided with a user interface such as a personal computer 11A, an external memory 11B such as a hard disk unit, and so on.

The optical defect-inspection apparatus 10 also includes a movable wafer stage 12, and a stage control unit 13 for moving vertically and horizontally the movable wafer stage 12 under control of the system control unit 11. A semiconductor wafer W such as a silicon wafer to be inspected is detachably set on the wafer stage 12. Note that a plurality of semiconductor chips (not shown) are already produced in a front surface of the silicon wafer W, and that the semiconductor chips are identical to each other.

Although not shown in FIG. 4, the optical defect-inspection apparatus 10 is provided with a wafer loading/unloading unit which is driven under control of the system control unit 11 so that the silicon wafer W can be automatically loaded on the wafer stage 12, and so the silicon wafer W can be automatically unloaded from the wafer stage 12.

Although not shown in FIG. 4, the optical defect-inspection apparatus 10 is also provided with an optical positioning unit which is driven under control of the system control unit 11. The optical positioning unit includes a CCD camera for photographing a positioning mark (not shown) formed on the silicon wafer W, and the CCD camera is immovably supported by a main frame (not shown) of the optical defect-inspection apparatus 10. A coordinate system is defined with respect to the main frame of the defect-inspection apparatus 10, and the system control unit 11 can positionally specify and recognize the silicon wafer W with respect to the coordinate system.

In short, the positioning mark photographed by the CCD camera is processed by the system control unit 11, and thus it is possible to position the silicon wafer W at a predetermined position with respect to the coordinate system by driving the stage control unit 13 under control of the system control system.

The optical defect-inspection apparatus 10 further includes an optical image-sensing unit 14 which is operated under control of the system control unit 11 so as to optically sense the semiconductor chips produced on the silicon wafer W.

The optical image-sensing unit 14 includes a light source 14A such as a laser light source for emitting a light beam LB, and an intensity of the light source 14A is adjustable by the system control unit 11.

Also, the optical image-sensing unit 14 includes an optical illumination system 14B having a condenser lens $14B_1$ and a half mirror $14B_2$ for directing the light beam LB toward the silicon wafer W, and a focusing lens system 14C for focusing the light beam LB on the silicon wafer W so that the silicon wafer W is illuminated with the focused light beam LB.

Although the focusing lens system 14C is represented by only one lens in FIG. 4, in reality, it includes a plurality of lenses, some of which is movable along an optical axis thereof, so that an optical power of the focusing lens system 14C can be varied. Namely, the focusing lens system 14C is suitably driven by the system control unit 11 so that a given optical power may be set in the focusing lens system. Also, by the setting of the optical power, a focal plane, on which the light beam LB is focused, is automatically defined.

Whenever the optical power of the focusing lens system 14C is varied, the wafer stage 12 is vertically moved by the stage control unit 13 with respect to the optical image-sensing unit 14 so that the silicon wafer W to be inspected is positioned in place with respect to the focal plane.

After the silicon wafer W to be inspected is positioned in place with respect to the focal plane, the wafer stage 12 is horizontally moved by driving the stage control unit 13 under control of the system control unit 11, so that the semiconductor chips on the silicon wafer W are scanned with the light beam LB.

The optical image-sensing unit 14 further includes an image sensor 14D such as a charge-coupled device (CCD) sensor, which is driven under control of the system control unit 11, and which receives the light beam LB reflected by the silicon wafer W through the half mirror $14B_2$ during the scanning of the silicon wafer W with the light beam LB. The image sensor 14D sequentially converts the received light beam LB into image signals.

The optical defect-inspection apparatus 10 further includes an image-processing unit 15 which is driven under control of the system control unit 11. The image-processing unit 15 includes an image-signal processing circuit 15A, a delay circuit 15B, an image-matching circuit 15C and an image comparing circuit 15D. Note that the image-processing unit 15 may be formed as a digital signal processor (DSP).

The image-signal processing circuit 15A contains an analog-to-digital (A/D) converter which receives the image signals from the image sensor 14D, and which sequentially converts the image signals into frames of digital image signals by the A/D converter. Then, in the image-signal processing circuit 15A, digital chip images of semiconductor chips on the silicon wafer W are sequentially produced based on the frame of digital image signal, and are output to both the delay circuit 15B and the image-matching circuit 15C.

While consecutive two digital chip images are output from the image-signal processing circuit 15A, the leading one of the consecutive digital chip images is temporarily held in the delay circuit 15B until the trailing one of the consecutive two-digital chip images is output from the image-signal processing circuit 15A, so that the respective leading and trailing ones of the consecutive two digital images are input from the delay circuit 15B and the image-signal processing circuit 15A to the image-matching circuit 15C.

In the image-matching circuit 15C, the consecutive digital chip images are matched with each other, and the matched digital chip images are output to the image-comparing circuit 15D in which the trailing one of the consecutive digital chip images is compared as a reference digital chip image with the leading one thereof to thereby produce a comparative chip image. The comparative chip image is fed to the system control unit 11 in which it is inspected whether or not there are defects in the trailing digital chip image based on the comparative chip image. The inspection results may be displayed together with the comparative chip images on the monitor of the personal computer 11A, if necessary, and may be stored in the external memory 11B, if necessary.

Thus, the inspection of the semiconductor wafer W is carried out by the optical defect-inspection apparatus 10 to determine whether or not each of the semiconductor chips has defects.

In the optical defect-inspection apparatus 10 of FIG. 4, when the optical power is set in the focusing lens system 14C, the focal plane, on which the light beam LB is focused, is automatically defined.

Usually, the focal plane can be regarded as being invariable. Nevertheless, in reality, the focal plane may be minutely shifted from the original position due to aging of the stage control unit 13, the focusing lens system 14C and so on, and due to environmental changes surrounding the optical defect-inspection apparatus 10, and the minute shift of the focal plane cannot be ignored when the defects to be detected on the silicon wafer W are very fine.

Thus, it is necessary to periodically and relatively carry out a positional adjustment of the silicon wafer W with respect to the focal plane defined by the focusing lens system 14C before the inspection of the silicon wafers W can be always properly carded out in the optical defect-inspection apparatus 10.

In the optical defect-inspection apparatus 10, when the positional adjustment of the silicon wafer W with respect to the focal plane of the focusing lens system 14C is carried out, a focus-adjustment wafer is used to prepare adjustment data for the positional adjustment of the silicon wafer W.

First Embodiment of Focus-Adjustment Wafer

Figure 5:
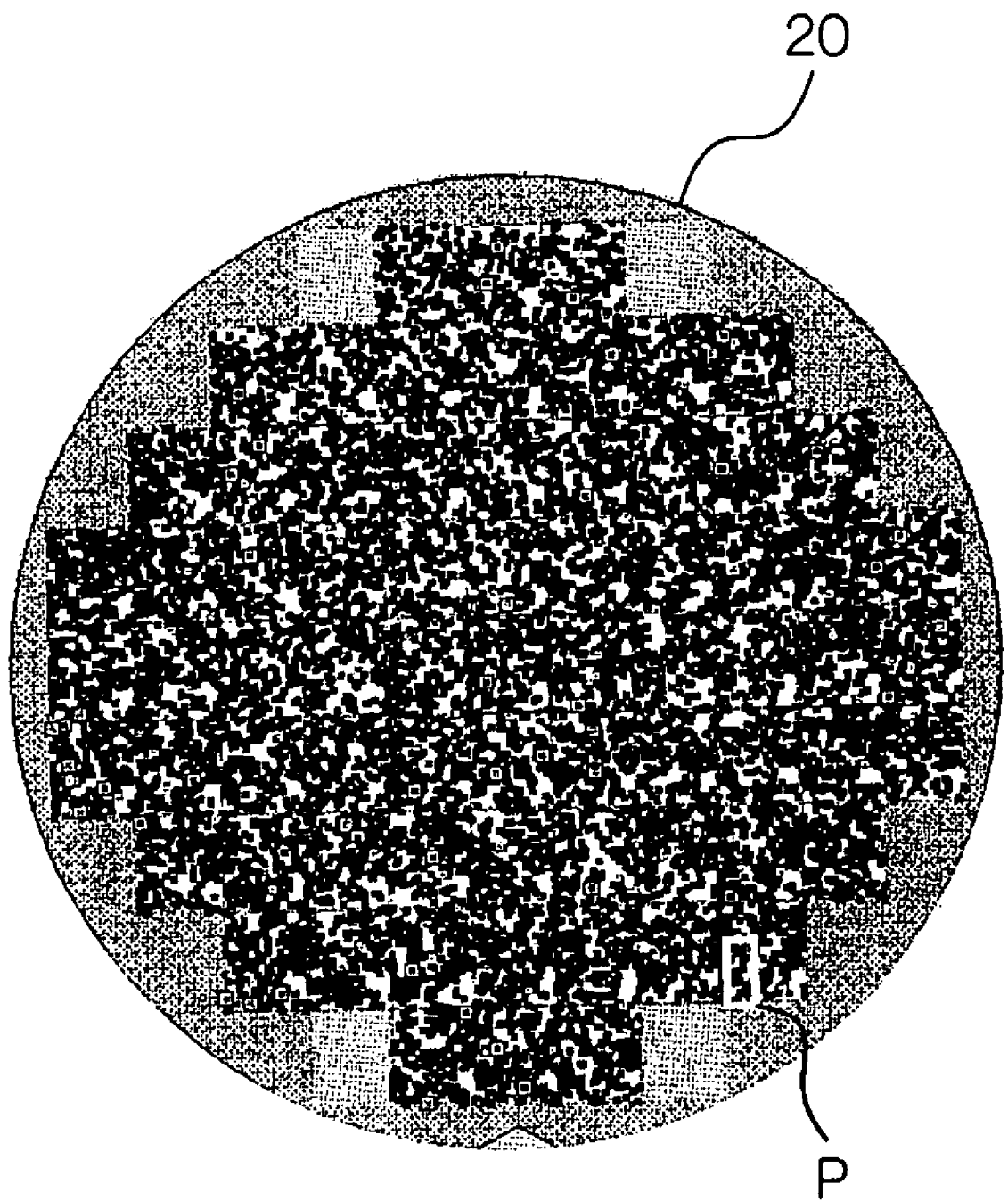
FIG. 5 is a plan view of a first embodiment of the focus-adjustment wafer used to carry out an adjustment of a focal plane of a focusing-lens system included in the defect-inspection apparatus of FIG. 4.

With reference to FIG. 5 which is a plan view showing a first embodiment of the focus-adjustment wafer, it is generally indicated by reference 20. The focus-adjustment wafer 20 has a plurality of chip areas formed on a front surface thereof, and the chip areas are identical to each other. Each of the chip areas has a plurality of solid patterns formed thereon, and a plurality of solid defects formed thereon between the solid patterns.

Figure 6A:
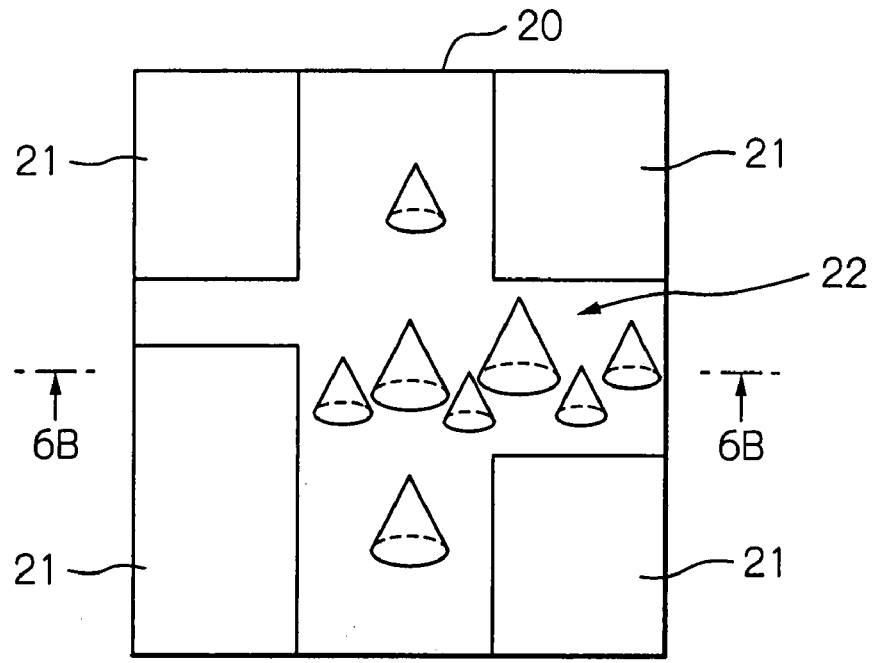
FIG. 6A is a partially-enlarged view showing a part of the focus-adjustment wafer of FIG. 5.

Referring to FIG. 6A which is a partially-enlarged view showing a part of a chip area, indicated by reference P in FIG. 5, the solid patterns are indicated by reference 21, and the solid defects are generally indicated by reference 22. Each of the solid patterns 21 is configured as a rectangular-like parallelepiped pattern, and each of the solid defects 22 is configured as a cone-shaped solid defect.

Note, in FIG. 6A, although each of the solid defects 22 should be illustrated as a circle, it is expediently shown in a perspective manner. Also, note, although not shown in FIG. 6A, the focus-adjustment wafer 20 has a similar positioning mark to that of the aforesaid silicon wafer W.

Figure 6B:
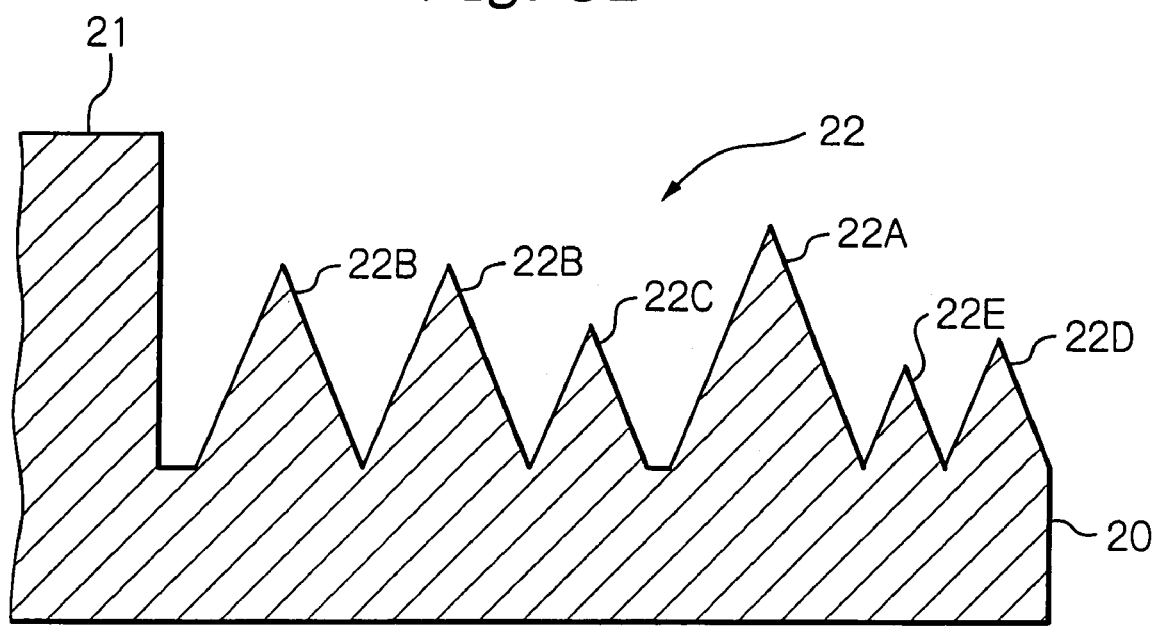
FIG. 6B is a cross-sectional view taken along the 6B-6B line of FIG. 6A.

Referring to FIG. 6B which is a cross-sectional view taken along the 6B-6B line of FIG. 6A, the solid defects 22 are sorted by size into five groups: a first group of solid defects 22A having the maximum size; a second group of solid defects 22B, only one of which is representatively shown, having a smaller size than that of the solid defect 22A; a third group of solid defects 22C, only one of which is representatively shown, having a smaller size than that of the solid defect 22B; a fourth group of solid defects 22D, only one of which is representatively shown, having a smaller size than that of the solid defect 22C; and a fifth group of solid defects 22E, only one of which is representatively shown, having a smaller size than that of the solid defect 22D.

Figure 7A:
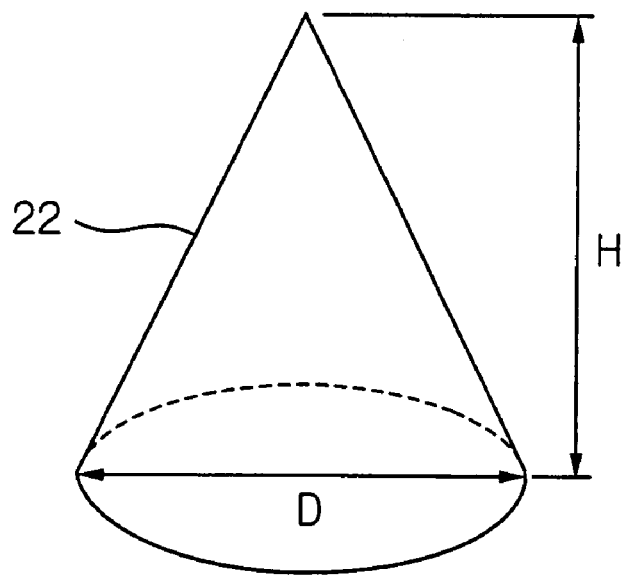
FIG. 7A is a perspective view representatively showing one of the solid defects formed on the focus-adjustment wafer of FIGS. 6A and 6B.

As shown in FIG. 7A which representatively shows one of the solid defects 22, the size of the solid defects 22 is defined as a diameter D of the bottom thereof, and each of the solid defects 22 has an individual height H defined as a distance between the bottom and the apex thereof. Preferably, the solid defects 22 have substantially the same apex angle, and the height H varies in accordance with the sizes or diameters D of the solid defects.

Figure 7B:
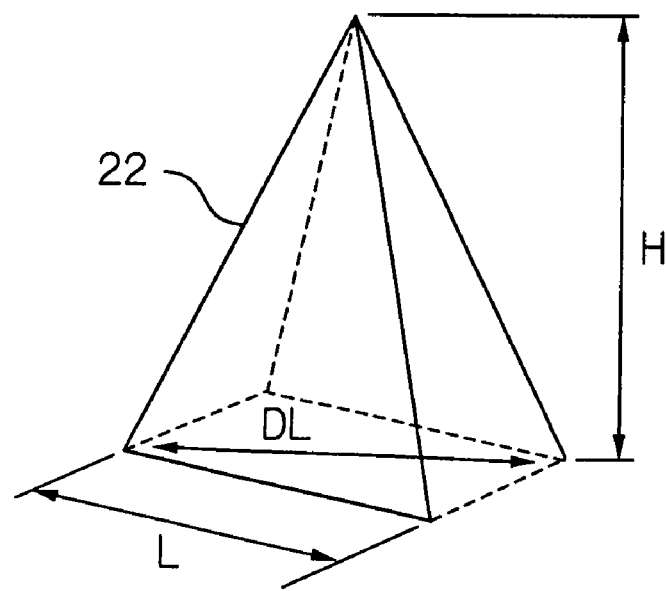
FIG. 7B is a perspective view of a modification of the solid defect of FIG. 7A.

As shown in FIG. 7B which is a perspective view showing a modification of the solid defect 22, each of the solid defects 22 may be configured as a pyramid-shaped solid defect, the size of the pyramid-shaped solid defect 22 may be as either a diagonal length DL of the bottom thereof or a length L of the longer side thereof. Also, similar to the case of FIG. 7A, preferably, the pyramid-shaped solid defects 22 have substantially the same apex angle, and the height H varies in accordance with the diagonal lengths DL or the long-side lengths L of the pyramid-shaped solid defects 22.

Referring again to FIG. 6B, in reality, the solid defects 22 have more than the aforesaid four sizes, and are randomly arranged on the surface of the focus-adjustment wafer 20 (see: FIG. 5). Also, the solid defects 22 are arranged at a density falling within a range between several/cm$^2$ and hundreds/cm$^2$. For example, the density range may be from 5/cm$^2$ to 10/cm$^2$.

For example, when it is assumed that the silicon wafer W to be inspected in the optical defect-inspection apparatus 10 of FIG. 4 has defects having sizes falling within a size range between 0.1 µm and 0.3 µm, the sizes of the solid defects 22 may fall within a size range between 0.05 µm and 0.5 µm, and the numbers of the solid defects 22, having the sizes falling within the range between 0.1 µm and 0.3 µm, are larger than those of the remaining solid defects 22.

In the size range between 0.1 µm and 0.3 µm, for the example, the focus-adjustment wafer 20 of FIG. 5 may be provided with 300 solid defects having the 0.12 µm size, 350 solid defects having the 0.14 µm size, 400 solid defects having the 0.16 µm size, 350 solid defects having the 0.18 µm size, 300 solid defects having the 0.20 μm size, 250 solid defects having the 0.22 μm size, and 200 solid defects having the 0.25 μm size. In this case, of course, a number of the solid defects 22 having the sizes smaller than 0.1 μm is smaller than 200, and a number of the solid defects 22 having the sizes larger than 0.3 μm is also smaller than 200.

In the above example, although the solid defects having the size of 0.16 μm is the maximum number (400), the solid defects having another size, for example, 0.25 μm, may be the maximum number. Further, the solid defects having the size 0.16 μm and the solid defects may be the maximum number. In short, the distribution of the defects 22 in the various defect sizes has at least one maximum value in the middle of the size range between 0.05 μm and 0.5 μm.

Explanation of Preparation of Adjustment Data

With reference to FIGS. 8A, 8B and 8C, each of which corresponds to FIG. 5B, how to prepare the adjustment data is explained below.

First, referring to FIG. 8A, the focus-adjustment wafer 20 is set in place on the wafer stage 12 of the optical defect-inspection apparatus 10 (see: FIG. 4), and a focal plane defined by the focusing lens system 14C is indicated by reference FP. As stated above, when the optical power of the focusing lens system 14C is set, the focal plane FP, on which the light beam LB should be focused, is automatically defined. Note, in FIG. 8A, it is supposed that the focal plane FP is shown at the original position indicated by "0".

When the focus-adjustment wafer 20 is inspected by the 10, the solid defect 22A is detected as a defect having the maximum size $D_{MAX}$, and the solid defect 22E is detected as a defect having the minimum size $D_{MIN}$.

Next, referring to FIG. 8B, the focal plane FP is upwardly shifted by a distance of +α from the original position "0" with respect to the focus-adjustment wafer 20 by downwardly moving the wafer stage 12. When the focus-adjustment wafer 20 is again inspected by the optical defect-inspection apparatus 10, the solid defect 22A is again detected as a defect having the maximum size $D_{MAX}$, and the solid defect 22D is detected as a defect having the minimum size $D_{MIN}$. Note that the solid defect 22E cannot be detected.

Next, referring to FIG. 8C, the focal plane FP is downwardly shifted by a distance of −α from the original position "0" with respect to the focus-adjustment wafer 20 by upwardly moving the wafer stage 12. When the focus-adjustment wafer 20 is further inspected by the optical defect-inspection apparatus 10, the solid defect 22A is again detected as a defect having the maximum size $D_{MAX}$ and the solid defect 22E is detected as a defect having the minimum size $D_{MIN}$.

As stated above, whenever the focal plane FP is shifted from the original position "0" (see: FIG. 8A), the inspection of the focus-adjustment wafer 20 is repeatedly carried out. At each of the inspections, a number of the defects, having a given size of, for example, 0.25 μm±β, is counted. Note that the value of β is suitably selected.

In reality, the inspections were carried out by the inventor, as explained with reference to FIGS. 8A, 8B and 8C.

Figure 9:
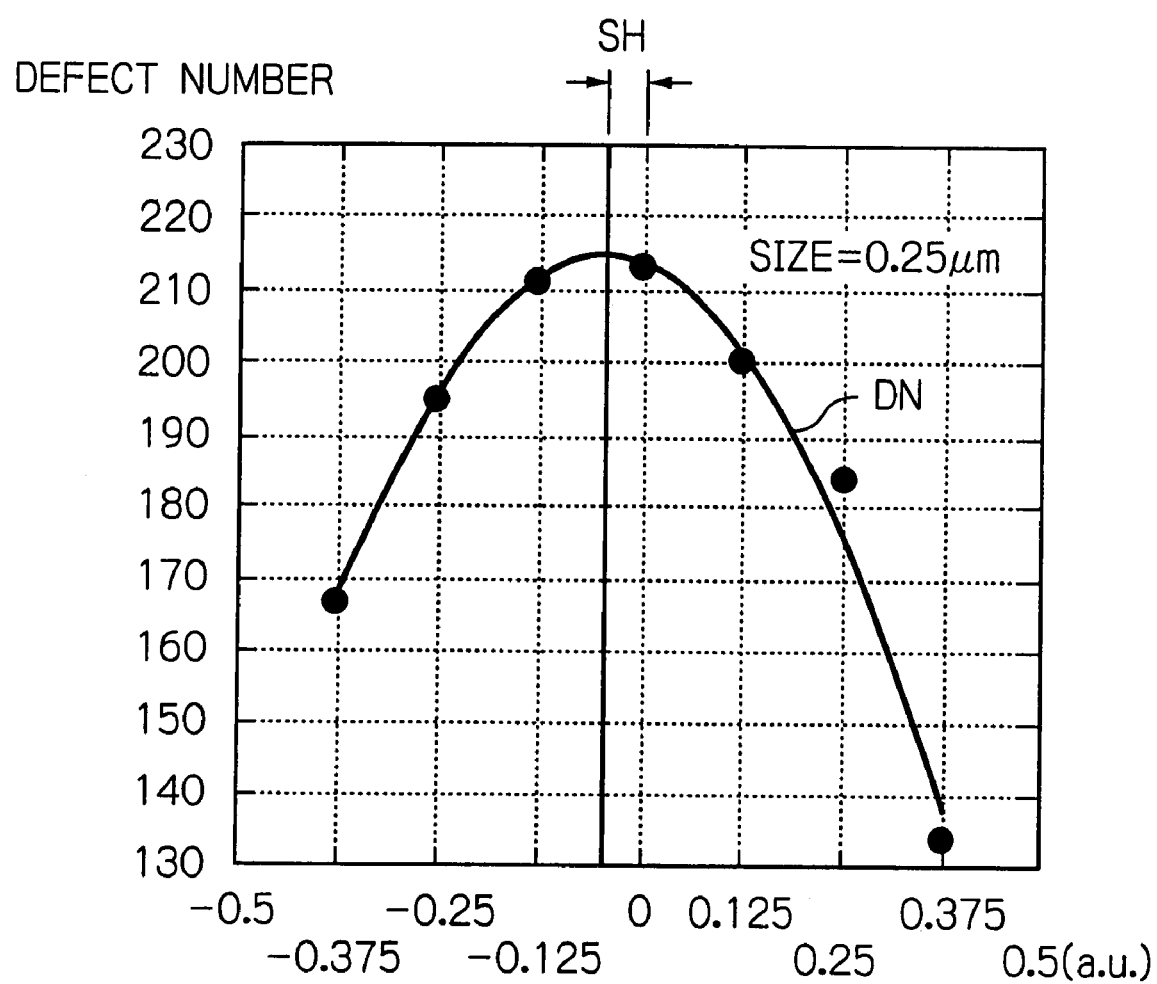
FIG. 9 is a graph showing a defect-number distribution which is obtained by repeating an inspection of the focus-adjustment wafer in the defect-inspection apparatus of FIG. 4.

Referring to a graph of FIG. 9, the results of the inspections are represented by a defect-number distribution DN. In this graph, the abscissa represents the positions at which the focal plane FP is shifted from the original position "0" (see: FIG. 8A), and the ordinate represents the number of defects having the size of about 0.25 μm, which are detected at each of the positions.

As shown in the graph of FIG. 9, when the focal plane FP was at the original position "0" (see: FIG. 8A), the number of the detected defects was 214.

When the focal plane FP was shifted upward from the original position "0" (see: FIG. 8A) by 0.125, the number of the detected defects was 200; when the focal plane FP was shifted upward from the original position "0" by 0.25, the number of the detected defects was 184; and when the focal plane FP was shifted upward from the original position "0" by 0.375, the number of the detected defects was 134.

On the other hand, when the focal plane FP was shifted downward from the original position "0" (see: FIG. 8A) by −0.125, the number of the detected defects was 211; when the focal plane FP was shifted upward from the original position "0" by −0.25, the number of the detected defects was 195; and when the focal plane FP was shifted upward from the original position "0" by −0.375, the number of the detected defects was 167.

As shown in the graph of FIG. 9, the peak value of the defect-number distribution DN is shifted from the original position "0" (see: FIG. 8A). This means that the original position "0" of the focusing lens system 14C (see: FIG. 4) has been shifted by a shift value SH for the reasons already stated. The shift value SH is used as a correction value for carrying out a focus-adjustment of the focusing lens system 14C when the silicon wafer W is inspected in the optical defect-inspection apparatus 10 (see: FIG. 4).

Two Defect-Inspection Apparatuses

Figure 10:
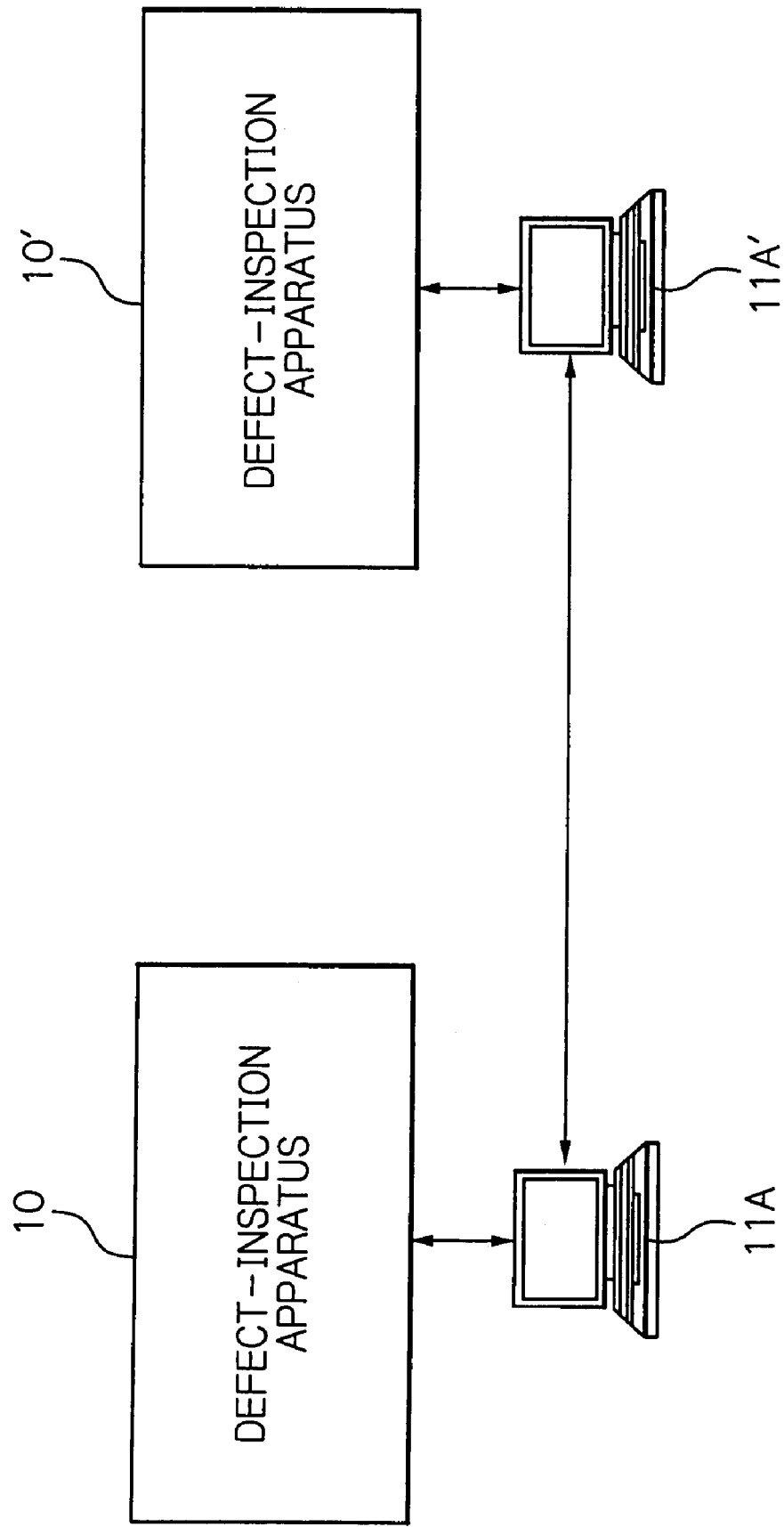
FIG. 10 is a block diagram of two defect-inspection apparatuses, one of which is defined as the old defect-inspection apparatus of FIG. 4 introduced earlier, the other apparatus being defined as a new defect-inspection apparatus introduced later.

Referring to FIG. 10 which is a block diagram of two optical defect-inspection apparatuses, reference 10 indicates the old optical defect-inspection apparatus (see: FIG. 4) introduced earlier, and reference 10' indicates a new optical defect-inspection apparatus introduced later. The new optical defect-inspection apparatus 10' is identical to the old optical defect-inspection apparatus 10. Thus, in FIG. 4, the elements of the new optical defect-inspection apparatus 10' are indicated by similar references primed.

As shown in FIG. 10, the personal computer 11A' of the new optical defect-inspection apparatus 10' is connected to a personal computer 11A of the old optical defect-inspection apparatus 10.

When the new optical defect-inspection apparatus 10' is introduced, it is preferable that various control parameters, various data and so on are used in common in the old and new optical defect-inspection apparatuses 10 and 10'. To this end, it is necessary to make focusing characteristics of the new optical defect-inspection apparatus 11' conform with those of the old optical defect-inspection apparatus 10.

Figure 11:
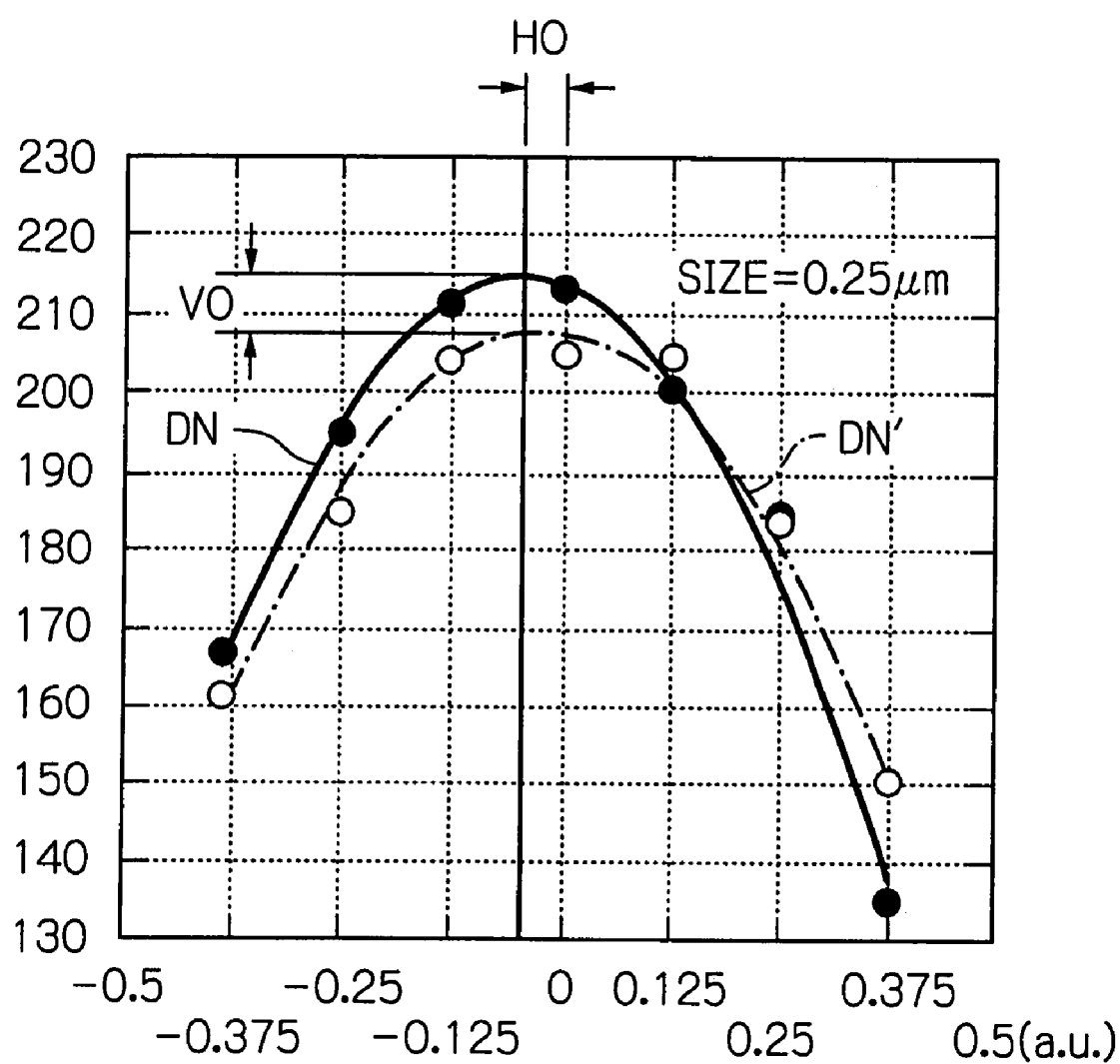
FIG. 11 is a similar graph to that of FIG. 9, showing a defect-number distribution, which is obtained by repeating an inspection of the focus-adjustment wafer in the new defect-inspection apparatus of FIG. 10, together with the defect-number distribution of FIG. 9.

In particular, referring to a graph of FIG. 11 which corresponds to the graph of FIG. 9, reference DN' indicates a defect-number distribution obtained by inspecting the focus-adjustment wafer 20 (see: FIG. 5) in the new optical defect-inspection apparatus 10' in substantially the same manner as stated above. As shown in the graph of FIG. 11, a peak value of the defect-number distribution DN' is vertically and horizontally offset from the peak value of the defect-number distribution DN obtained by the old optical defect-inspection apparatus 10.

In the new optical defect-inspection apparatus 10', the personal computer 11A' previously asks the personal computer 11A to be fed the peak value of the defect-number distribution DN, and the peak value of the defect-number distribution DN is input to the system control unit 11' of the new optical defect-inspection apparatus 10' through the personal computer 11A'.

As shown in the graph of FIG. 11, in the system control unit 11', a vertical offset value V0 and a horizontal offset value H0 are calculated based on both the peak value of the defect-number distribution DN' and the peak value of the defect-number distribution DN. The vertical offset value V0 and the horizontal offset value H0 are used as correction values for shifting the defect-number distribution DN' so as to conform with the defect-number distribution DN.

Thus, the focusing characteristics of the old and new optical defect-inspection apparatuses 10 and 10' conform with each other, whereby it is possible to use the various control parameters, the various data and so on in common.

Focus-Adjustment Data Preparation Method

Figure 12:
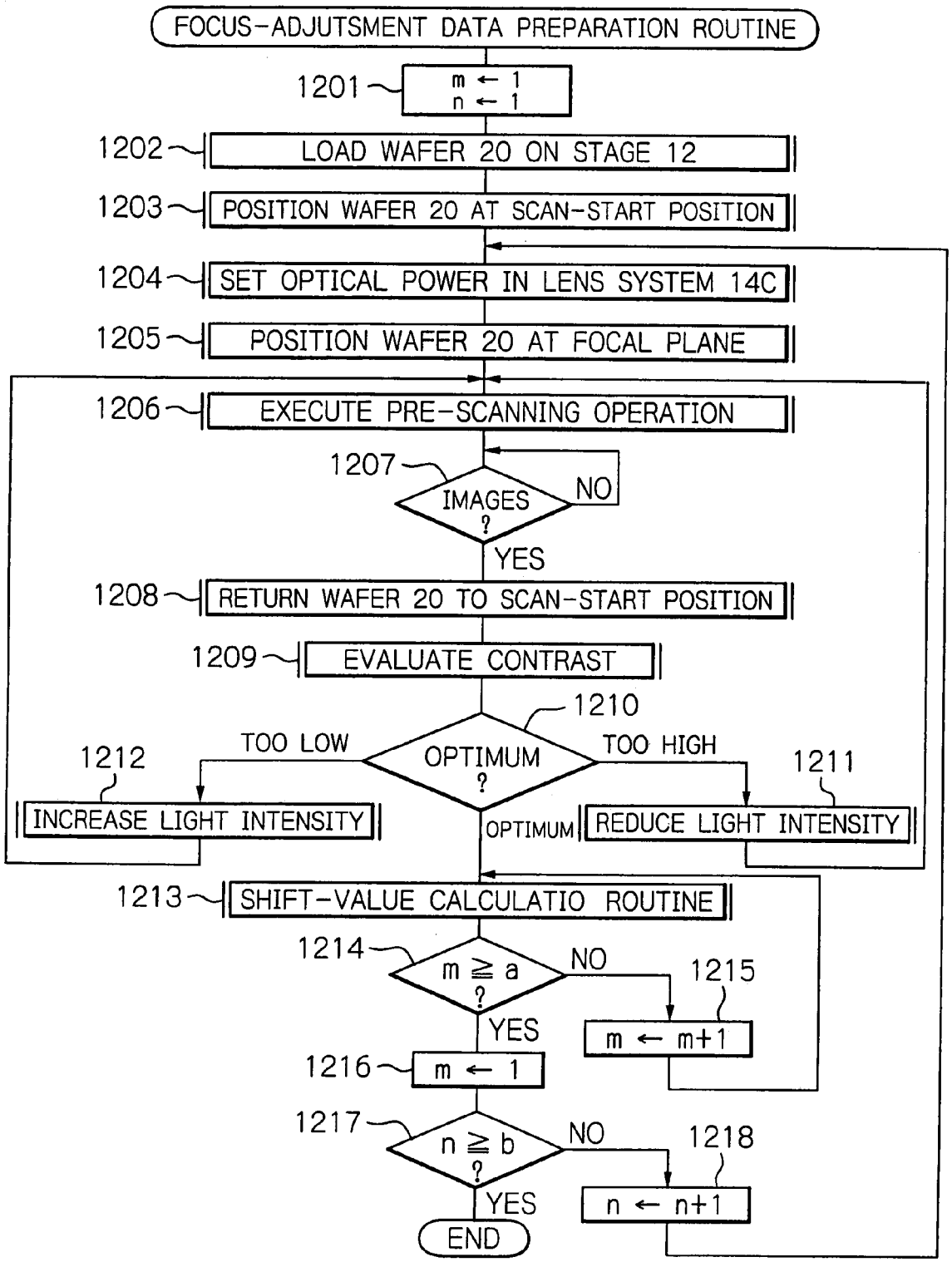
FIG. 12 is a flowchart of a focus-adjustment data preparation routine executed in a system control unit of the defect-inspection apparatus of FIG. 4.

With reference to FIG. 12 showing a flowchart of a focus-adjustment data preparation routine which is executed by the system control unit 11 of FIG. 4, a focus-adjustment data preparation method according to the present invention is explained below.

Before the execution of the focus-adjustment data preparation routine, various data, such as a defect size (pixel size) $DS_m$ to be detected from the focus-adjustment wafer 20 (see: FIG. 5), an optical power $OP_n$ to be set in the focusing lens system 14C, a scanning-range size for defining an area of the focus-adjustment wafer 20 to be scanned with the light beam LB, and so on, are already input to the system control unit 11 through the personal computer 11A, and are stored in the RAM of the system control unit 11.

For the defect size $DS_m$, at least one value is selected from the above-mentioned range between 0.1 µm and 0.3 µm.

Also, for the optical power $OP_n$, at least one value is selected among numerical values of 0.12, 0.16, 0.20, 0.25, 0.39, 0.62 and 1.25 which are previously prepared in the personal computer 11A. Note that the numerical values are inherent in the optical defect-inspection apparatus 10, and that the selection of the numerical values is carried out in accordance with the defect size $DS_m$.

Further, the area of the focus-adjustment wafer 20 (see: FIG. 5), which is defined by the scanning-range size, may correspond to, for example, four chip areas on the focus-adjustment wafer 20.

At step 1201, counter values "m" and "n" are initialized to be "1".

At step 1202, the focus-adjustment wafer 20 is loaded and set on the wafer stage 12 by driving the aforesaid loading/unloading unit (not shown) of the optical defect-inspection apparatus 10 under control of the system control unit 11.

At step 1203, the focus-adjustment wafer 20 is positioned at a predetermined position or scan-start position with respect to the coordinate system of the optical defect-inspection apparatus 10 by driving the stage control unit 13 under control of the system control unit 11, using the aforesaid optical positioning unit (not shown) of the optical defect-inspection apparatus 10.

At step 1204, the focusing lens system 14C is driven under control of the system control unit 11 so that the optical power $OP_n$ is set in the focusing lens system 14C. At this time, a focal plane FP (see: FIG. 8A), on which the light beam LB should be focused, is automatically defined at an original position "0" (see: FIG. 8A).

At step 1205, the wafer stage 12 is vertically moved by driving the stage control unit 13, so that the focus-adjustment wafer 20 is positioned at a given position with respect to the original position "0" of the focal plane FP (see: FIG. 8A).

At step 1206, a pre-scanning operation for regulating the intensity of the optical source 14A is executed. Namely, the four chip areas, which are included in the area defined by the aforesaid scanning-range size, are scanned with the light beam LB.

During the pre-scanning operation, the image sensor 14D sequentially feeds image signals to the image-processing unit 15, and the image signals are processed in substantially the same manner as stated above. Namely, four digital chip images are sequentially produced based on the image signals in the image-signal processing circuit 15A, and consecutive two digital chip images are matched with each other in the image-matching circuit 15C. Then, the matched digital chip images are output to the image-comparing circuit 15D in which a comparative chip image is produced based on the matched chip images, and the comparative chip image is fed to the system control unit 11.

Note that a number of the comparative chip images produced in the image-comparing circuit 15D is three because the four chip areas on the focus-adjustment wafer 20 are scanned with the light beam LB, as stated above. Also, note that each of the comparative chip images has solid pattern images corresponding to the solid patterns 21 (see: FIGS. 6A and 6B).

At step 1207, it is monitored whether the three comparative chip images have been fed from the image-comparing circuit 15D to the system control unit 11. When it is confirmed that the three comparative chip images have been fed to the system control unit 11, the control proceeds to step 1208, in which the focus-adjustment wafer 20 is returned to the scan-start position by driving the stage control unit 13 under control of the system control unit 11.

At step 1209, a contrast is evaluated between the solid patterns 21 and the background based on the comparative chip images. Then, at step 1210, it is determined whether the contrast is optimum.

At step 1210, when it is determined that the contrast is too high, the control proceeds from step 1210 to step 1211, in which the intensity of the light source 14A is reduced. Then, the control returns to step 1206, in which the routine comprising steps 1206, 1207, 1208, 1209, 1210 and 1211 is repeated.

On the other hand, at step 1210, when it is determined that the contrast is too low, the control proceeds from step 1210 to step 1212, in which the intensity of the light source 14A is increased. Then, the control returns to step 1206, in which the routine comprising steps 1206, 1207, 1208, 1209, 1210 and 1212 is repeated.

At step 1210, when it is determined that the contrast is optimum, the control proceeds from step 1210 to step 1213, in which a shift-value calculation routine is executed to calculate a shift value SH (see: FIG. 9). Note that the shift-value calculation routine is explained with reference to FIG. 13.

After the calculation of the shift value SH is completed, the control proceeds to step 1214, in which it is determined whether the counter value "m" has reached a predetermined number "a". The number "a" corresponds to a number of defect sizes $DS_m$ to be detected. Namely, at step 1214, there is another defect size $DS_m$ to be detected.

If m<a, the control proceeds from step 1214 to step 1215, in which the counter value "m" is incremented by "1". Then, the control returns to step 1213, in which the shift-value calculation routine is again executed.

At step 1214, if m≧a, the control proceeds from step 1215 to step 1216, in which the counter value "m" is initialized to be "1".

At step 1217, it is determined whether the counter value "n" has reached a predetermined natural number "b" The number "b" corresponds to a number of optical power $OP_n$ to be set in the focusing lens system 14C. Namely, at step 1217, there is another optical power $OP_n$ to be set in the focusing lens system 14C.

If n<b, the control proceeds from step 1217 to step 1218, in which the counter value "n" is incremented by "1". Then, the control returns to step 1204, and thus the routine comprising steps 1205 to 1218 is repeated.

At step 1217, if n≧b, the focus-adjustment data preparation routine ends.

Figure 13:
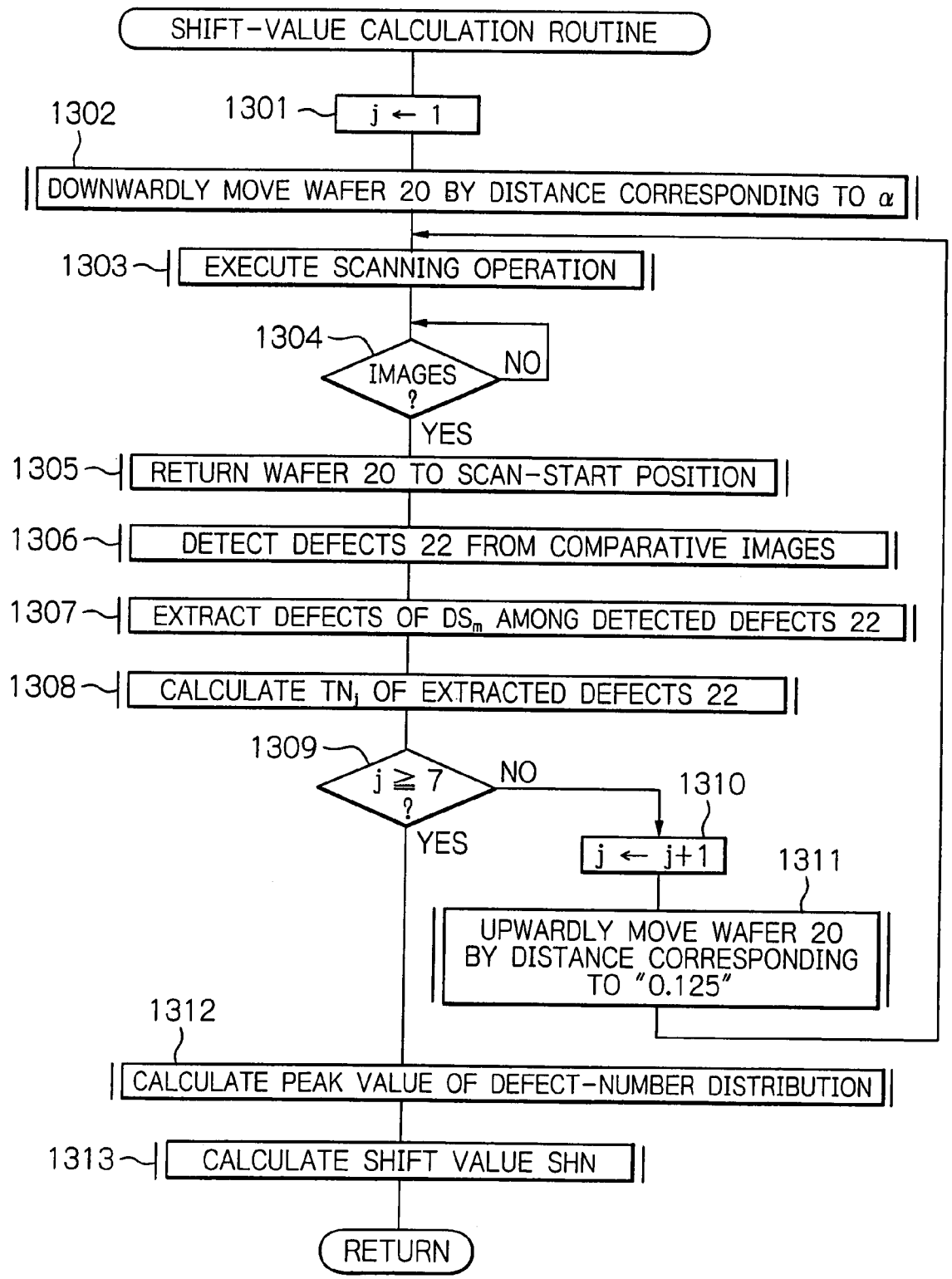
FIG. 13 is a flowchart of a shift-value calculation routine executed in the focus-adjustment data preparation routine of FIG. 12.

Referring to FIG. 13, the shift-value calculation routine, executed in step 1213 of the focus-adjustment data preparation routine of FIG. 12, is explained below.

At step 1301, a counter value "j" is initialized to be "1".

At step 1302, the stage control unit 13 is driven under control of the system control unit 11 so that the focus-adjustment wafer 20 on the wafer stage 12 is downwardly moved from the original position "0" (see: FIG. 8A) by a distance corresponding to the absolute value of α (see: FIG. 308B). At this time, the focus-adjustment wafer 20 is positioned at a position corresponding to the numerical value −0.375 on the abscissa of the graph of FIG. 9.

At step 1303, a scanning operation for detecting the solid defects 22 (see: FIGS. 8A to 8C) is executed. Namely, the chip areas, which are included in the area defined by the aforesaid scanning-range size, are scanned with the light beam LB.

During the scanning operation, the image sensor 14D sequentially feeds image signals to the image-processing unit 15, and the image signals are processed in substantially the same manner as stated above. Namely, four digital chip images are sequentially produced based on the image signals in the image-signal processing circuit 15A, and consecutive two digital chip images are matched with each other in the image-matching circuit 15C. Then, the matched chip images are output to the image-comparing circuit 15D in which a comparative chip image is produced based on the matched chip images, and the comparative chip image is fed to the system control unit 11.

Note that a number of the comparative chip images produced in the image-comparing circuit 15D is three because the four chip areas on the focus-adjustment wafer 20 are scanned with the light beam LB, as stated above. Also, note that each of the comparative chip images has solid defect images corresponding to the solid defects 22 (see: FIGS. 6A and 6B).

At step 1304, it is monitored whether the three comparative chip images have been fed from the image-comparing circuit 15D to the system control unit 10. When it is confirmed that the three comparative chip images have been fed to the system control unit 11, the control proceeds to step 1305, in which the focus-adjustment wafer 20 is returned to the scan-start position by driving the stage control unit 13 under control of the system control unit 11.

At step 1306, the solid defects 22 (see: FIGS. 8A, 8B and 8C) are detected from the comparative chip images. Then, at step 1307, solid defects having the size $DS_m \pm \beta$ are extracted among the solid defects 22. Subsequently, at step 1308, a total number $TN_j$ of the extracted solid defects 22 is calculated, and is stored in the RAM of the system control unit 11.

At step 1309, it is determined whether the counter value "j" has reached "7". If j<7, the control proceeds from step 1309 to step 1310, in which the counter value "j" is incremented by "1". Then, at step 1311, the focus-adjustment wafer 20 on the wafer stage 12 is upwardly moved by a distance corresponding to the numerical value of 0.125 by driving the wafer control stage 13 under control of the system control unit 11, so that the focus-adjustment wafer 20 is positioned at a position corresponding to the numerical value −0.25 on the abscissa of the graph of FIG. 9.

Subsequently, the control returns to step 1303, and the routine comprising steps 1303 to 1311 is repeated until the counter value "j" reaches "7" at step 1309, i.e. until the seven total numbers $TN_j$ are obtained at the positions corresponding to the respective numerical values −0.375, −0.25, −0.125, 0.0, 0.125, 0.25 and 0.375 on the abscissa of the graph of FIG. 9.

Note that the seven total numbers $TN_j$, which are stored in the RAM of the system control unit 11, define a defect-number distribution DN (see: FIG. 9).

When it is confirmed that the counter value "j" has reached "7", the control proceeds from step 1309 to step 1312, in which a peak value of the defect-number distribution DN (see: FIG. 9) is calculated based on the seven total numbers $TN_j$. Then, at step 1313, a shift value SH (see: FIG. 9) is calculated based on the peak value of the defect-number distribution DN, and the control returns to step 1215 of the focus-adjustment data preparation routine of FIG. 12.

Note that the shift value SH is used as a correction value for carrying out a focus-adjustment of the focusing lens system 14C when the silicon wafer W is inspected in the optical defect-inspection apparatus (see: FIG. 4).

The new optical defect-inspection apparatus 10' of FIGS. 4 and 10 is provided with a program for executing substantially the same focus-adjustment data preparation routine as that of FIG. 12, except that an offset-value calculation routine is executed in step 1214 of FIG. 12 as a substitute for the shift-value calculation routine of FIG. 13.

Figure 14:
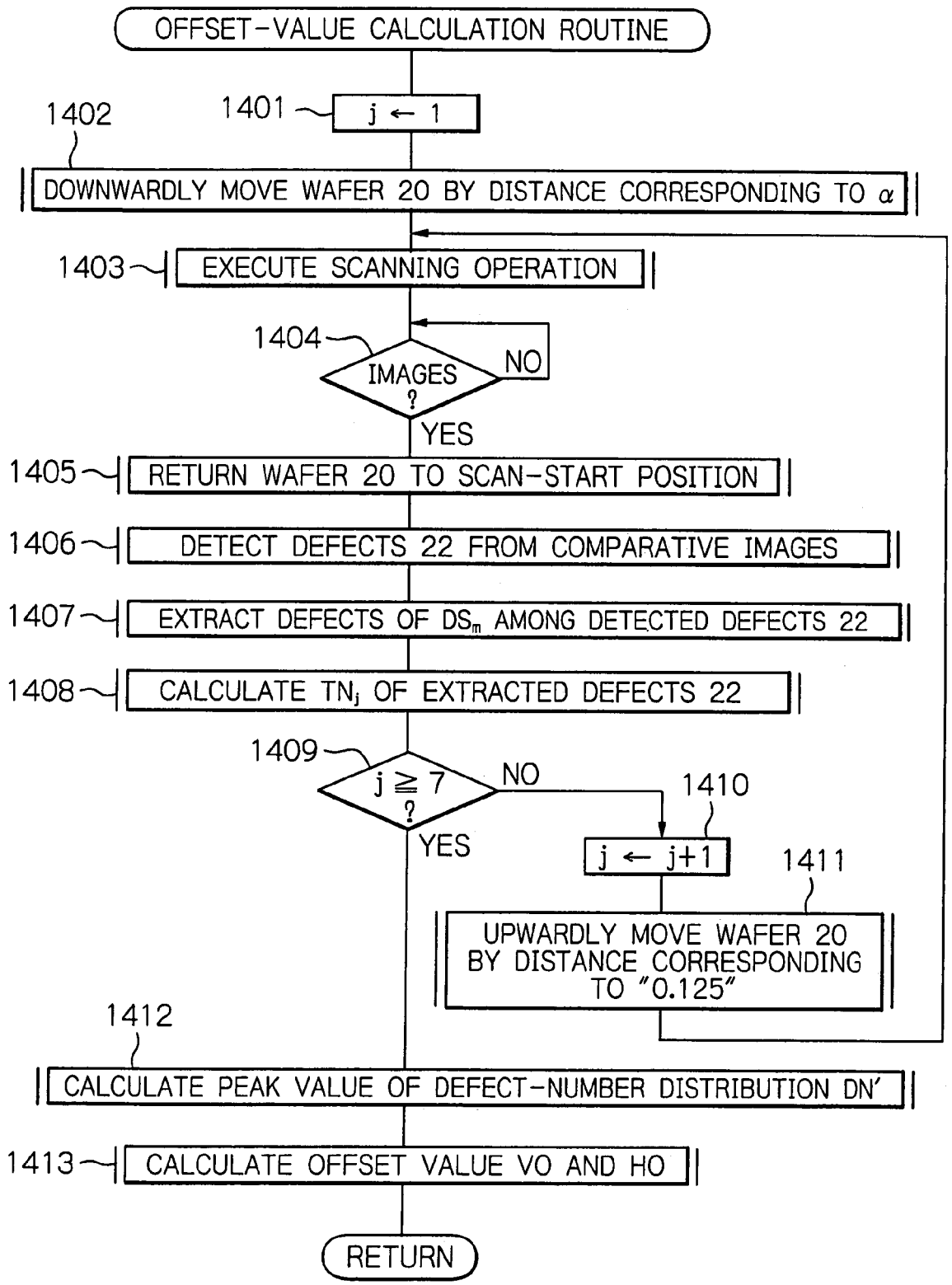
FIG. 14 is a flowchart of an offset-value calculation routine executed in the focus-adjustment data preparation routine of FIG. 12.

Referring to FIG. 14, the offset-value calculation routine executed in the system control unit 11' of the new optical defect-inspection apparatus 10', is explained below.

Note that the personal computer 11A' previously asks the personal computer 11A to be fed the peak value of the defect-number distribution DN, and that the peak value of the defect-number distribution DN is already input to the system control unit 11' of the new optical defect-inspection apparatus 10' through the personal computer 11A'.

At step 1401, a counter value "j" is initialized to be "1".

At step 1402, the stage control unit 13' is driven under control of the system control unit 11' so that the focus-adjustment wafer 20 on the wafer stage 12' is downwardly moved from the original position "0" (see: FIG. 8A) by a distance corresponding to the absolute value of α (see: FIG. 8B). At this time, the focus-adjustment wafer 20 is positioned at a position corresponding to the numerical value −0.375 on the abscissa of the graph of FIG. 11.

At step 1403, a scanning operation for detecting the solid defects 22 (see: FIGS. 8A to 8C) is executed. Namely, the four chip areas, which are included in the area defined by the aforesaid scanning-range size, are scanned with the light beam LB'.

During the scanning operation, the image sensor 14D' sequentially feeds image signals to the image-processing unit 15', and the image signals are processed in substantially the same manner as stated above. Namely, four digital chip images are sequentially produced based on the image signals in the image-signal processing circuit 15A', and consecutive two digital chip images are matched with each other in the image-matching circuit 15C'. Then, the matched chip images are output to the image-comparing circuit 15D' in which a comparative chip image is produced based on the matched chip images, and the comparative chip image is fed to the system control unit 11'.

Note that a number of the comparative chip images produced in the image-comparing circuit 15D' is three because the four chip areas on the focus-adjustment wafer 20 are scanned with the light beam LB', as stated above. Also, note that each of the comparative chip images has solid defect images corresponding to the solid defects 22 (see: FIGS. 6A and 6B).

At step 1404, it is monitored whether the three comparative chip images have been fed from the image-comparing circuit 15D' to the system control unit 10'. When it is confirmed that the comparative chip images have been fed to the system control unit 11', the control proceeds to step 1405, in which the focus-adjustment wafer 20 is returned to the scan-start position by driving the stage control unit 13' under control of the system control unit 11'.

At step 1406, the solid defects 22 (see: FIGS. 8A, 8B and 8C) are detected from the comparative chip images. Then, at step 1407, solid defects having the size $DS_m±β$ are extracted among the solid defects 22. Subsequently, At step 1408, a total number $TN_j$ of the extracted solid defects is calculated, and is stored in the RAM of the system control unit 11'.

At step 1409, it is determined whether the counter value "j" has reached "7". If j<7, the control proceeds from step 1409 to step 1410, in which the counter value "j" is incremented by "1". Then, at step 1411, the focus-adjustment wafer 20 on the wafer stage 12' is upwardly moved by a distance corresponding to the numerical value of 0.125 by driving the wafer control stage 13' under control of the system control unit 11', so that the focus-adjustment wafer 20 is positioned at a position corresponding to the numerical value −0.25 on the abscissa of the graph of FIG. 11'.

Subsequently, the control returns to step 1403, and the routine comprising steps 1403 to 1411 is repeated until the counter value "j" reaches "7" at step 1409, i.e. until the seven total numbers $TN_j$ are obtained at the positions corresponding to the respective numerical values −0.375, −0.25, −0.125, 0.0, 0.125, 0.25 and 0.375 on the abscissa of the graph of FIG. 11.

Note that the seven total numbers $TN_j$, which are stored in the RAM of the system control unit 11', define a defect-number distribution DN' (see: FIG. 11).

When it is confirmed that the counter value "j" has reached "7", the control proceeds from step 1409 to step 1412, in which a peak value of the defect-number distribution DN' (see: FIG. 11) is calculated based on the seven total numbers $TN_j$. Then, at step 1413, a vertical offset value V0 and a horizontal offset value H0 (see: FIG. 11) are calculated based on both the peak value of the defect-number distribution DN' and the peak value of the defect-number distribution DN, and the control returns to step 1215 of the focus-adjustment data preparation routine of FIG. 12.

Note that the vertical offset value V0 and the horizontal offset value H0 are used as correction values for shifting the defect-number distribution DN' so as to conform with the defect-number distribution DN, whereby it is possible to use the various control parameters, the various data and so on in common in the old and new optical defect-inspection apparatuses 10 and 11'.

Focus-Adjustment Wafer Manufacturing Method

Figure 15A:
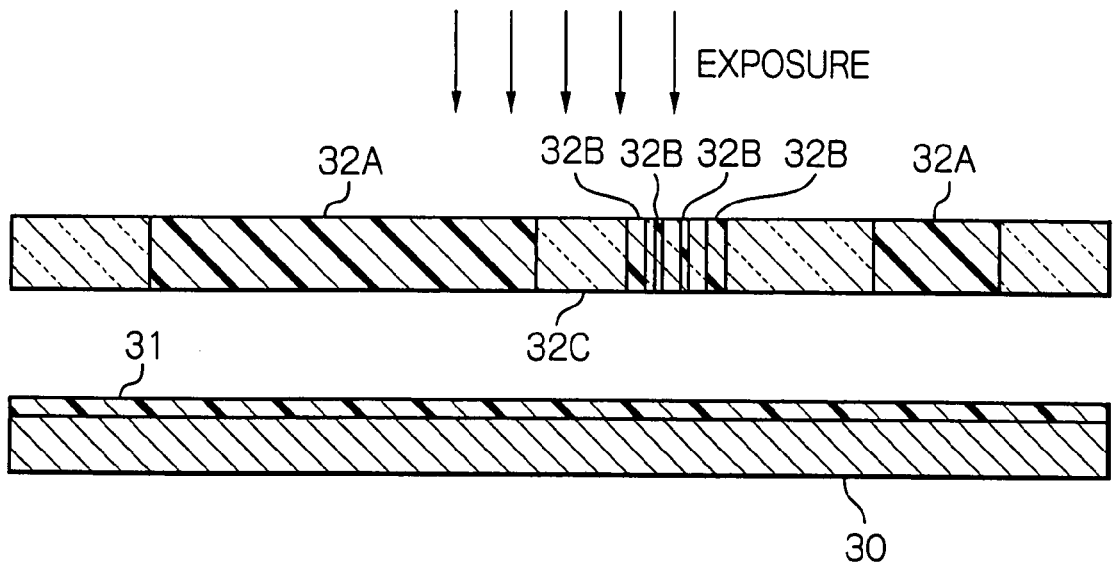
FIGS. 15A, 15B and 15C are cross-sectional views for explaining a method for manufacturing the focus-adjustment wafer of FIG. 5.
Figure 15B:
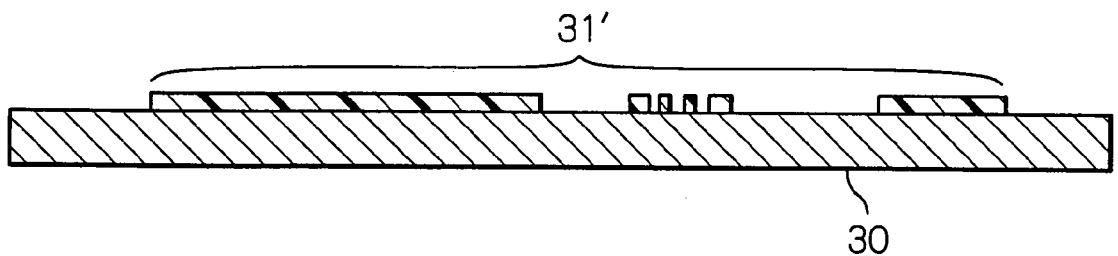
Figure 15C:
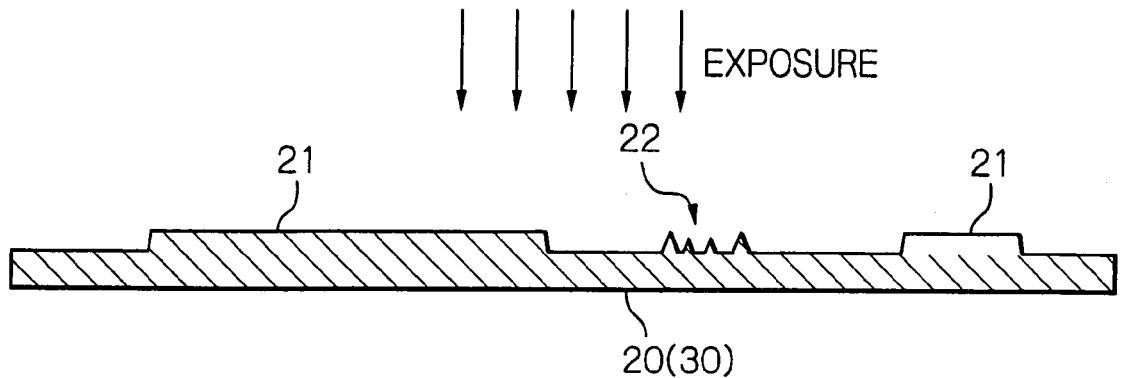

With reference to FIGS. 15A, 15B and 15C which are cross-sectional views, a method for manufacturing the focus-adjustment wafer 20 of FIG. 5 is explained below.

First, referring to FIG. 15A, a wafer substrate 30, which may be a silicon wafer blank, is prepared, and a photoresist layer 31 is formed on the wafer substrate 30. On the other hand, a photomask or reticle 32 is prepared, and has a plurality of shade areas 32A for forming the solid patterns 21 (see: FIGS. 6A and 6B), and a plurality of shade areas 32B for forming the cone-shaped solid patterns 22 (see: FIGS. 6A and 6B), with the remaining area of the reticle 32 being defined as a transparent area 32C.

Figure 16A:
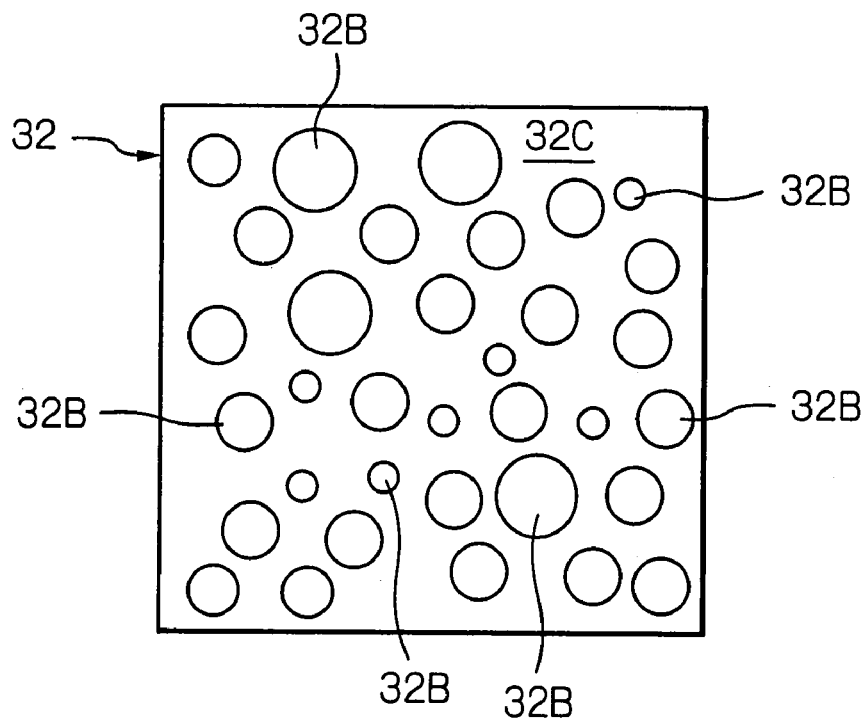
FIG. 16A is a partially-enlarged plan view of a reticle of FIG. 15A.

Referring to FIG. 16A which is a partially-enlarged plan view of a part of the reticle 32, the shade areas 32B are defined as circular areas having various sizes. In this case, each of the solid defects 22 is configured as the cone-shaped solid defect 22 (see: FIG. 7A).

Figure 16B:
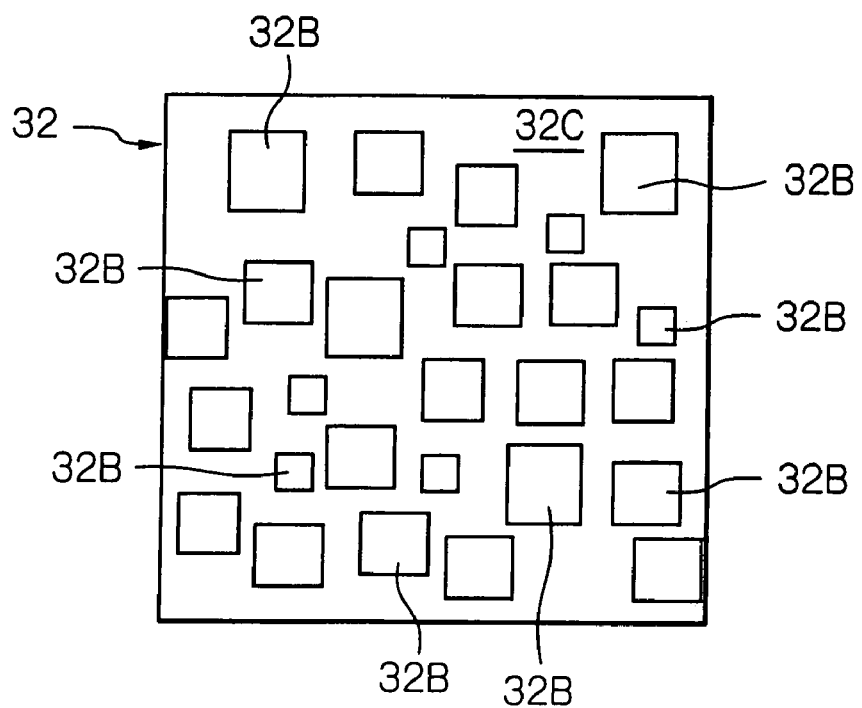
FIG. 16B is another partially-enlarged plan view of the reticle of FIG. 15A.

Also, referring to FIG. 16B which is a partially-enlarged plan view of a part of the reticle 32, the shade areas 32B are defined as square areas having various sizes. In this case, each of the solid defects 22 is configured as the pyramid-shaped solid defect 22 (see: FIG. 7B).

Referring again to FIG. 15A, the reticle 32 is positioned in place above the wafer substrate 30 with the photoresist layer 31, and then the photoresist layer 31 is subjected to an exposure process by using light rays such as ultraviolet rays, as symbolically represented by arrows. Namely, only an area of the photoresist layer 31, which corresponds to the transparent area 32C, is exposed with the ultraviolet rays. Subsequently, the photoresist layer 31 is subjected to a development process.

Next, referring to FIG. 15B, after the development process is completed, the photoresist layer 31 is subjected to a washing process in which only the exposed area of the photoresist layer 31 is removed so that a photoresist mask 31' is defined.

Next, referring to FIG. 15C, the wafer substrate 30 is subjected to an anisotropic etching process such as an ion-beam etching process, as symbolically represented by arrows, so that the focus-adjustment wafer 20 having the solid patterns 21 and the solid defects 22 is manufactured from the wafer substrate 30. Of course, the conditions of the ion-beam etching process are suitably set in a conventional manner so that the solid defects 22 are configured as either the cone-shaped solid defects (see: FIG. 7A) or the pyramid-shaped solid defects (see: FIG. 7B).

In the above-mentioned focus-adjustment wafer manufacturing method, although the solid patterns 21 and the solid defects 22 are directly formed in the wafer substrate 30, the solid patterns 21 and the solid defects 22 may be formed in a suitable layer such as a silicon oxide layer, a metal layer or the like, which is formed on the wafer substrate 30.

Note that, during a manufacturing process of semiconductor devices, a large number of defects may be accidentally formed on a semiconductor wafer, and that there is a case where such a semiconductor wafer may be utilized as the focus-adjustment wafer 20.

Second Embodiment of Focus-Adjustment Wafer

Figure 17:
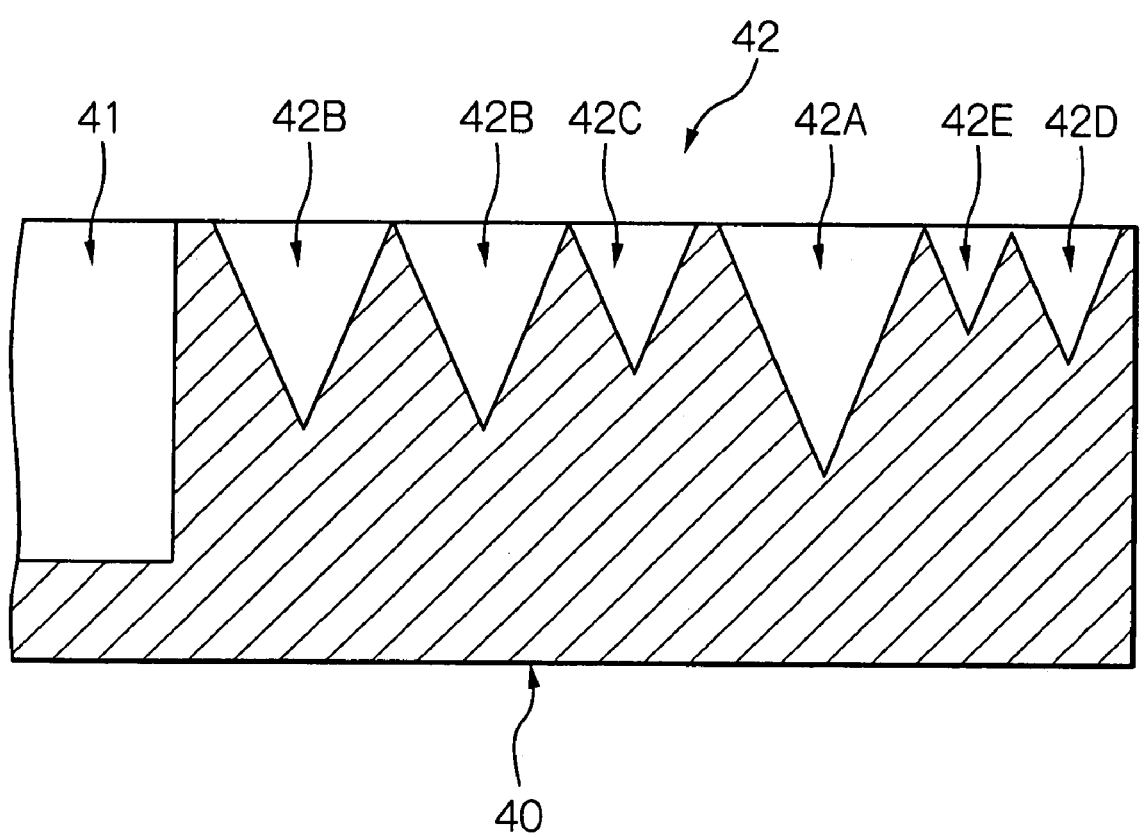
FIG. 17 is a cross-sectional view, corresponding to FIG. 6B, showing a second embodiment of the focus-adjustment wafer according to the present invention.

With reference to FIG. 17 which corresponds to FIG. 6B, a second embodiment of the focus-adjustment wafer according to present invention is generally indicated by reference 40.

The focus-adjustment wafer 40 has a plurality of chip areas formed on a front surface thereof, and the chip areas are identical to each other. Each of the chip areas has a plurality of hollow patterns 41 formed therein, and only one of the hollow patterns 41 is representatively and partially illustrated. Also, each of the chip areas has a plurality of hollow defects 42 formed therein.

In the second embodiment, the hollow pattern 42 may be configured as a rectangular-like parallelepiped hollow pattern, and each of the hollow defects 42 may be configured as either a cone-shaped hollow defect or a pyramid-shaped hollow defect.

Similar to the focus-adjustment wafer 20 of FIG. 6B, the hollow defects 42 are sorted by size into five groups: a first group of hollow defects 42A having the maximum size; a second group of hollow defects 42B, only one of which is representatively shown, having a smaller size than that of the solid defect 42A; a third group of hollow defects 22C, only one of which is representatively shown, having a smaller size than that of the hollow defect 42B; a fourth group of hollow defects 42D, only one of which is representatively shown, having a smaller size than that of the hollow defect 42C; and a fifth group of hollow defects 42E, only one of which is representatively shown, having a smaller size than that of the hollow defect 42D.

Thus, the focus-adjustment wafer 40 is substantially identical to the focus-adjustment wafer 20 of FIG. 6B except that the hollow pattern 41 is substituted for the solid pattern 21, and that the hollow defects 42 are substituted for the solid defects 22.

Also, the focus-adjustment wafer 40 can be manufactured by a similar method to that of FIGS. 15A, 15B and 15C, using a reversed reticle to the reticle 32 (FIG. 15A). Namely, when the reticle 32 of FIG. 15A is defined as a positive reticle, the reversed reticle is defined as a negative reticle.

Third Embodiment of Focus-Adjustment Wafer

Figure 18:
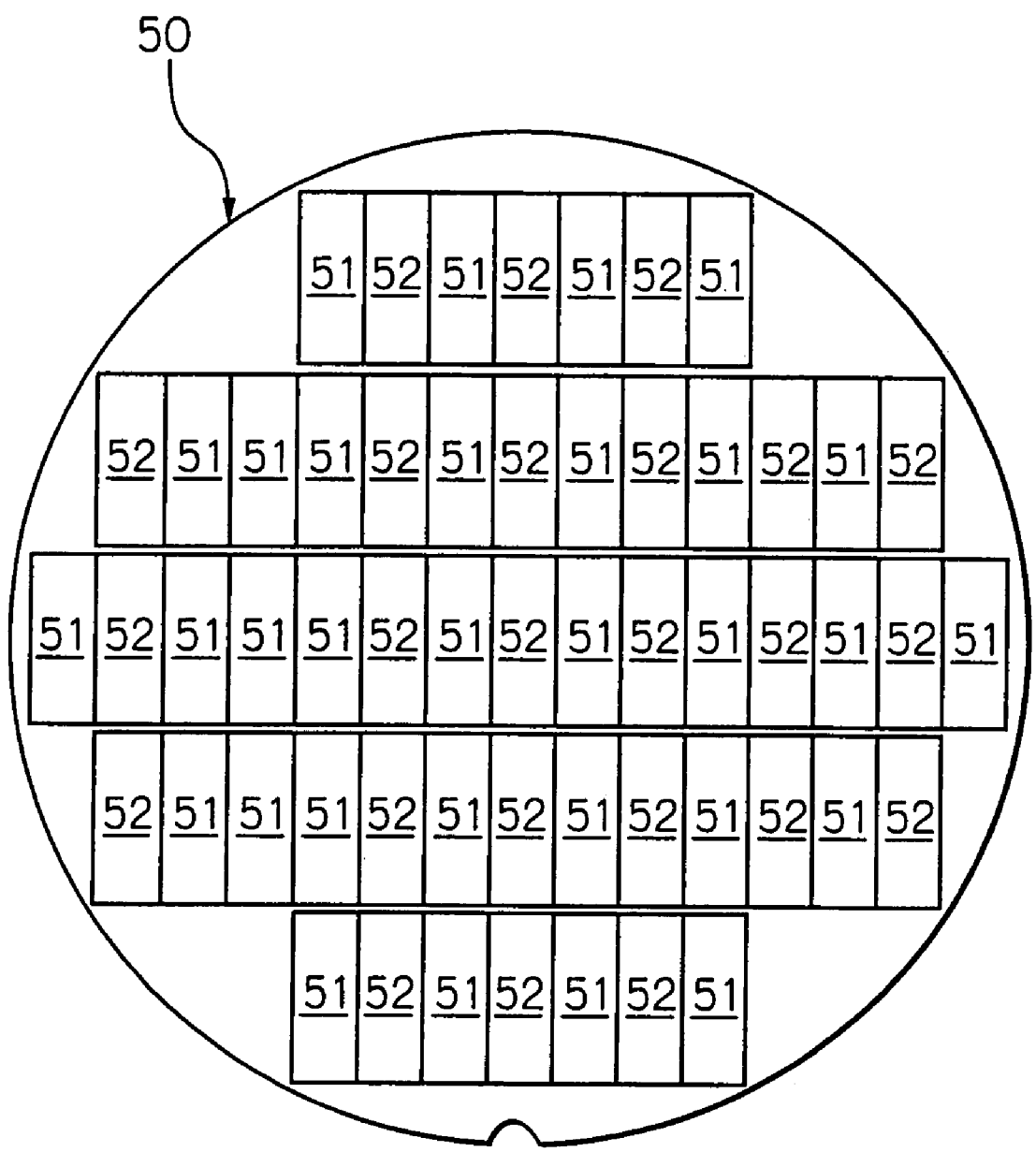
FIG. 18 is a plan view of a third embodiment of the focus-adjustment wafer according to the present invention.

With reference to FIG. 18 which is a plan view of a third embodiment of the focus-adjustment wafer according to the present invention, it is generally indicated by reference 50.

The focus-adjustment wafer 50 has a plurality of chips areas 51 and a plurality of chips area 52, which are formed on a front surface thereof, with the chip areas 51 having the same size as that of the chip areas 52. The chips 51 and 52 are alternately arranged side by side so as to define five rows, and each of the chip areas 52 is sandwiched between the adjacent chip areas 51. Also, the chip areas 51 are aligned with each other so as to define eight columns, and the chips areas 52 are aligned with each other so as to define seven columns.

Figure 19A:
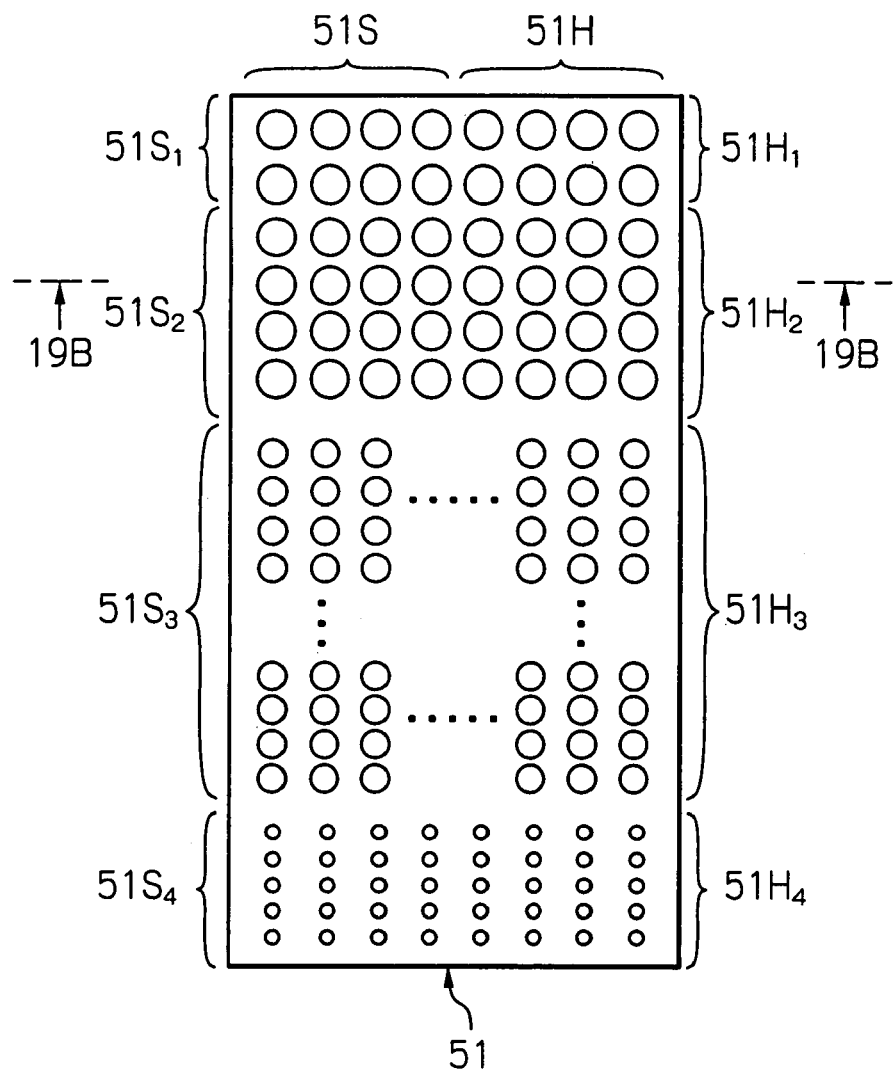
FIG. 19A is a partially enlarged plan view showing one of chip areas defined on the focus-adjustment wafer of FIG. 18.

Referring to FIG. 19A which is an partially-enlarged plan view showing one of the chip areas 51 on the focus-adjustment wafer 50, the chip area 51 has a plurality of solid patterns 51S formed thereon, and a plurality of hollow patterns 51H formed therein.

The solid patterns 51S are sorted by size into four groups: a first group of solid patterns $51S_1$ having the maximum size; a second group of solid patterns $51S_2$ having a smaller size than that of the solid patterns $51S_1$; a third group of solid patterns $51S_3$ having a smaller size than that of the solid patterns $51S_2$; and a fourth group of solid patterns $51S_4$ having a smaller size than that of the solid patterns $51S_3$. In each of the groups, the solid patterns $51S_1$, $51S_2$, $51S_3$ and $51S_4$ are arranged in a matrix manner.

The hollow patterns 51H are also sorted by size into four groups: a first group of hollow patterns $51H_1$ having the maximum size; a second group of hollow patterns $51H_2$ having a smaller size than that of the hollow patterns $51H_1$; a third group of hollow patterns $51H_3$ having a smaller size than that of the hollow patterns $51H_2$; and a fourth group of hollow patterns $51H_4$ having a smaller size than that of the hollow patterns $51H_3$. In each of the groups, the hollow patterns $51H_1$, $51H_2$, $51H_3$ and $51H_4$ are arranged in a matrix manner.

Figure 19B:
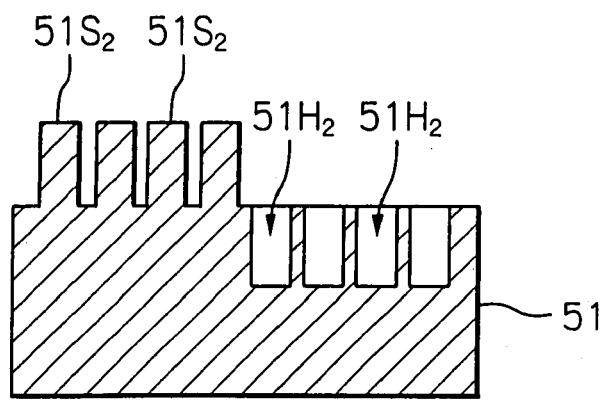
FIG. 19B is a cross-sectional view taken along the 19B-19B line of FIG. 19B.

As representatively shown in FIG. 19B which is a cross-sectional view taken along the line 19B-19B of FIG. 19A, each of the solid patterns $51S_1$, $51S_2$, $51S_3$ and $51S_4$ is configured as a circular column, and each of the hollow patterns $51H_1$, $51H_2$, $51H_3$ and $51H_4$ is configured as a circular bore. Also, the size of the solid patterns $51S_1$ is the same as that of the solid patterns $51H_1$; the size of the solid patterns $51S_2$ is the same as that of the solid patterns $51H_2$; the size of the solid patterns $51S_3$ is the same as that of the solid patterns $51H_3$; and the size of the solid patterns $51S_4$ is the same as that of the solid patterns $51H_2$.

Referring again to FIG. 19A, a number of the solid patterns $51S_3$ is maximum; a number of the solid patterns $51S_4$ is smaller than that of the solid patterns $51S_3$; a number of the solid patterns $51S_2$ is smaller than that of the solid patterns $51S_4$; and a number of the solid patterns $51S_1$ is minimum.

Similarly, a number of the hollow patterns $51H_3$ is maximum; a number of the hollow patterns $51H_4$ is smaller than that of the hollow patterns $51H_3$; a number of the hollow patterns $51H_2$ is smaller than that of the hollow patterns $51H_4$; and a number of the hollow patterns $51H_1$ is minimum.

Figure 20A:
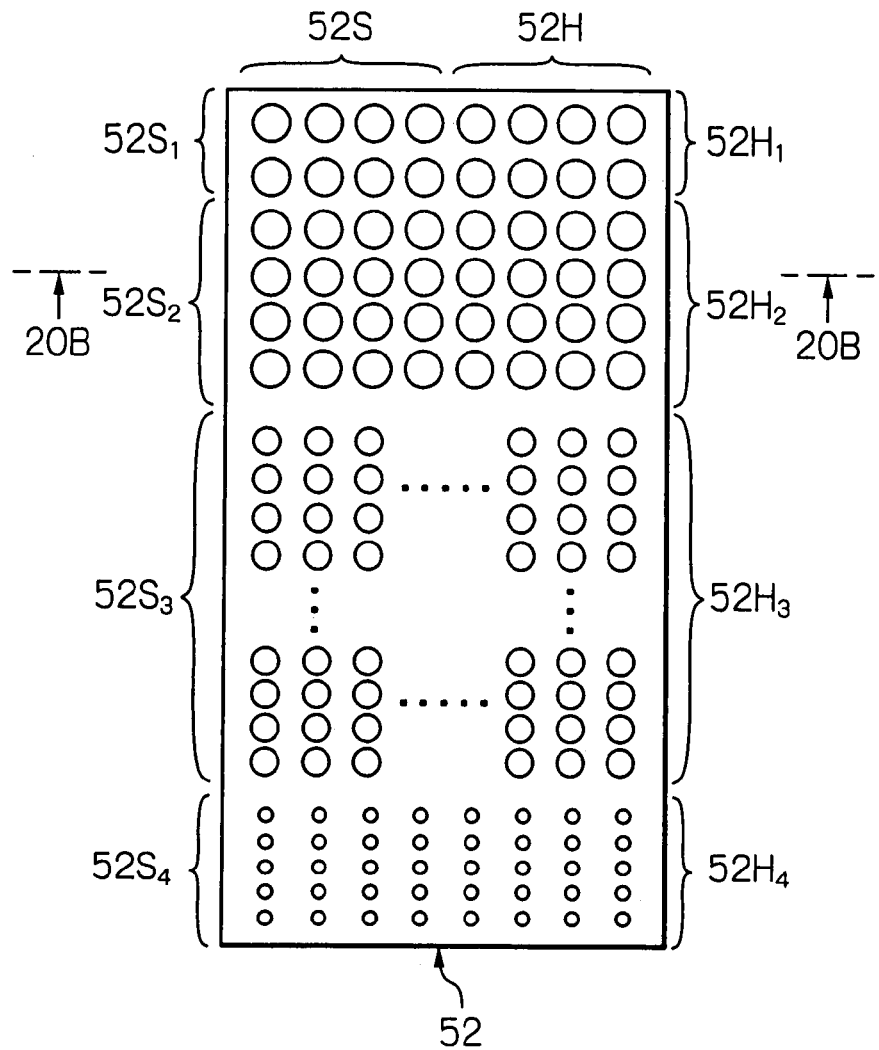
FIG. 20A is a partially-enlarged plan view showing another chip area formed on the focus-adjustment wafer of FIG. 18.

Referring to FIG. 20A which is an partially-enlarged plan view showing one of the chip areas 52 on the focus-adjustment wafer 50, the chip area 52 has a plurality of solid defects 52S formed thereon, and a plurality of hollow defects 52H formed therein.

The solid defects 52S are sorted by size into four groups: a first group of solid defects $52S_1$ having the same size as the diameter of the solid patterns $51S_1$ (see: FIG. 19A); a second group of solid defects $52S_2$ having the same size as the diameter of the solid patterns $51S_2$ (see: FIG. 19A); a third group of solid defects $52S_3$ having the same size as the diameter of the solid patterns $51S_3$ (see: FIG. 19A); and a fourth group of solid defects $52S_4$ having the same size as the diameter of the solid patterns $51S_4$ (see: FIG. 19A). The solid defects 52S are arranged on the chips area 52 in substantially the same manner as the solid patterns 51S (see: FIG. 19A).

The hollow defects 52H are also sorted by size into four groups: a first group of hollow defects $52H_1$ having the same size as the diameter of the hollow defects $51H_1$ (see: FIG. 19A); a second group of hollow defects $52H_2$ having the same size as the diameter of the hollow defects $51H_2$ (see: FIG. 19A); a third group of hollow defects $52H_3$ having the same size as the diameter of the hollow defects $51H_3$ (see: FIG. 19A); and a fourth group of hollow defects $52H_4$ having the same size as the diameter of the hollow defects $51H_4$ (see: FIG. 19A). The hollow defects 52H are arranged on the chips area 52 in substantially the same manner as the hollow patterns 51H (see: FIG. 19A).

Figure 20B:
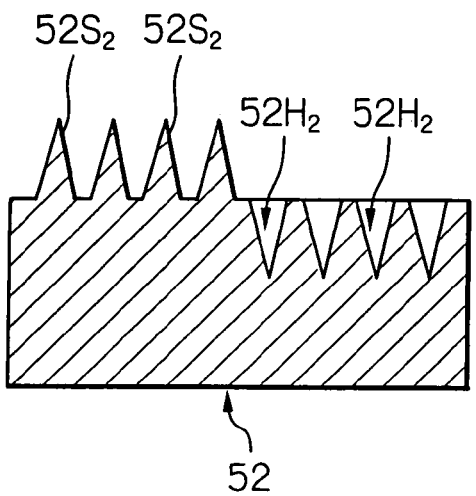
FIG. 20B is a cross-sectional view taken along the 20B-20B line of FIG. 20A.

As representatively shown in FIG. 20B which is a cross-sectional view taken along the line 20B-20B of FIG. 20A, each of the solid defects $52S_1$, $52S_2$, $52S_3$ and $52S_4$ is configured as a cone-shaped solid defect, and each of the hollow defects $52H_1$, $52H_2$, $52H_3$ and $52H_4$ is configured as a cone-shaped hollow defect.

In the focus-adjustment wafer 50 of FIG. 18, the chip areas 51 having the solid patterns 51S and the hollow patterns 51H are used when the intensity of the optical source 14A (14A') of FIG. 4 is regulated. Namely, when the pre-scanning operation is executed in step 1206 of FIG. 12, some of the chip areas 51 are scanned with the light beam LB (LB') so that the optimum contrast can be obtained.

Also, when the scanning operation is executed in either step 1303 of FIG. 13 or step 1403 of FIG. 14, first, one of the chip areas 51 is scanned with the light beam LB; then, a chip area 52 adjacent to the scanned chip area 51 is scanned with the light beam LB or LB'; and subsequently a chip area 51 adjacent to the scanned chip area 52 is scanned with the light beam LB or LB'. Namely, the chip area 51 and the chip area 52 are alternately scanned with the light beam LB or LB', and a digital chip image derived from the chip area 51 is compared as a reference digital chip image with a digital chip image derived from the chip area 52 in the image-comparing circuit 15D or 15D' (see: FIG. 4), to thereby detect the defects on the latter digital chip image (52).

The focus-adjustment wafer 50 of FIG. 18 can be also manufactured by using the method as stated with reference to FIGS. 15A, 15B and 15C.

Also, in the focus-adjustment wafer 50 of FIG. 18, each of the solid defects 52S (see: FIGS. 20A and 20B) may be configured as a pyramid-shaped solid defect, and each of the hollow defects 52H (see: FIGS. 20A and 20B) may be configured as a pyramid-shaped hollow defect. In this case, of course, each of the solid patterns 51S (see: FIGS. 19A and 19B) is formed as a square column having the same size as that of the bottom of the pyramid-shaped solid defect 52S, and each of the hollow patterns 51H (see: FIGS. 19A and 19B) is formed as a square bore having the same size as that of the bottom of the pyramid-shaped hollow defect 52H.

Finally, it will be understood by those skilled in the art that the foregoing description is of preferred embodiments of the wafer, and that various changes and modifications may be made to the present invention without departing from the spirit and scope thereof.

The invention claimed is:

1. A method for preparing focus-adjustment data for a focusing lens system of an optical defect-inspection apparatus, said method comprising:
   positioning a wafer having a plurality of defects in place with respect to a focal plane defined by said focusing lens system;
   optically and electronically detecting the plurality of defects on said wafer;
   extracting a number of defects having a predetermined size among the plurality of defects;
   counting the number of defects having the predetermined size as defect-number data;
   repeating said positioning, said detecting, said extracting, and said counting whenever said focus-adjustment wafer is relatively shifted from said focal plane by a predetermined distance to be a different focus value;
   producing a defect-number distribution based on said defect-number data thus obtained;
   calculating a peak value of said defect-number distribution; and
   calculating a vertical offset value by comparing said peak value with a peak value of a defect-number distribution obtained in a similar manner to said method in an optical defect-inspection apparatus which is identical to said optical defect-inspection apparatus.

2. A focus-adjustment wafer used in an optical defect-inspection apparatus to carry out a focus-adjustment of a focusing lens system of the optical defect-inspection apparatus, said focus-adjustment wafer comprising:
   a wafer substrate comprising a plurality of first chip areas defined thereon; and
   a plurality of defects formed on or in each of said first chip areas on said wafer substrate,
   wherein said plurality of defects has various sizes falling within a size range,
   wherein a distribution of the plurality of defects in said various sizes has at least one maximum value in a middle of said size range, and
   wherein each of said defects comprises a pyramid-shaped defect.

3. The focus-adjustment wafer as set forth in claim 2, wherein said size range is from about 0.05 μm to about 0.5 μm.

4. The focus-adjustment wafer as set forth in claim 2, wherein said plurality of defects is formed on or in said wafer substrate at a density in a range between several/cm$^2$ and hundreds/cm$^2$.

5. The focus-adjustment wafer as set forth in claim 2, wherein said pyramid-shaped defect comprises a solid defect on each of said first chip areas.

6. The focus-adjustment wafer as set forth in claim 2, wherein said pyramid-shaped defect comprises a hollow defect in each of said first chip areas.

7. The focus-adjustment wafer as set forth in claim 2, further comprising a plurality of patterns formed on or in at least one of said plurality of first chip areas on said wafer substrate.

8. The focus-adjustment wafer as set forth in claim 7, wherein each of said patterns comprises a rectangular-like parallelepiped pattern.

9. The focus-adjustment wafer as set forth in claim 8, wherein said rectangular-like parallelepiped pattern comprises a solid pattern on each of said first chip areas.

10. The focus-adjustment wafer as set forth in claim 8, wherein said rectangular-like parallelepiped pattern comprises a hollow pattern on each of said first chip areas.

11. The focus-adjustment wafer as set forth in claim 2, further comprising:
    said wafer substrate further comprising a plurality of second chip areas defined thereon; and
    a plurality of patterns formed on or in each of said second chip areas on said wafer substrate.

12. The focus-adjustment wafer as set forth in claim 11, wherein said plurality of first chip areas and said plurality of second chip areas are alternately arranged side by side.

13. A focus-adjustment wafer used in an optical defect-inspection apparatus to carry out a focus-adjustment of a focusing lens system of the optical defect-inspection apparatus, said focus-adjustment wafer comprising:
    a wafer substrate comprising a plurality of first chip areas and a plurality of second chip areas defined thereon;
    a plurality of defects formed on or in each of said first chip areas on said wafer substrate; and
    a plurality of patterns formed on or in each of said second chip areas on said wafer substrate,
    wherein each of said patterns is configured as a circular column,
    wherein the plurality of defects on each of the first chip areas is configured as a cone-shaped defect having a size equivalent to a diameter of said circular column,
    wherein said plurality of defects has various sizes falling within a size range,
    wherein a distribution of the plurality of defects in said various sizes has at least one maximum value in a middle of said size range;
    wherein a portion of said plurality of defects comprises a solid defect,
    wherein a remaining portion of said plurality of defects comprises a hollow defect,
    wherein a portion of said plurality of patterns comprises a solid pattern, and
    wherein a remaining portion of said plurality of patterns comprises a hollow pattern.

* * * * *